(12) United States Patent
Savaides et al.

(10) Patent No.: US 9,463,147 B2
(45) Date of Patent: *Oct. 11, 2016

(54) HAIR TREATMENT AND REVITALIZING COMPOSITION AND METHODS

(71) Applicant: ZOTOS INTERNATIONAL, INC., Darien, CT (US)

(72) Inventors: Andrew Savaides, Norwalk, CT (US); Rushi Tasker, Trumbull, CT (US); Komal Ladd, Danbury, CT (US); Mona Vaidya, Little Ferry, NJ (US)

(73) Assignee: Zotos International, Inc., Darien, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/028,107

(22) Filed: Sep. 16, 2013

(65) Prior Publication Data

US 2014/0014130 A1    Jan. 16, 2014

Related U.S. Application Data

(63) Continuation-in-part of application No. 13/656,286, filed on Oct. 19, 2012, now Pat. No. 9,283,156.

(60) Provisional application No. 61/618,276, filed on Mar. 30, 2012.

(51) Int. Cl.
| | |
|---|---|
| *A61K 8/21* | (2006.01) |
| *A61Q 5/02* | (2006.01) |
| *A61Q 5/06* | (2006.01) |
| *A61Q 5/12* | (2006.01) |
| *A45D 7/00* | (2006.01) |
| *A45D 7/06* | (2006.01) |
| *A61Q 5/04* | (2006.01) |

(52) U.S. Cl.
CPC . *A61K 8/21* (2013.01); *A45D 7/00* (2013.01); *A45D 7/06* (2013.01); *A61Q 5/02* (2013.01); *A61Q 5/04* (2013.01); *A61Q 5/06* (2013.01); *A61Q 5/12* (2013.01); *A45D 2007/002* (2013.01)

(58) Field of Classification Search
None
See application file for complete search history.

(56) References Cited

U.S. PATENT DOCUMENTS

| | | | |
|---|---|---|---|
| 4,919,920 A * | 4/1990 | Devos | 424/61 |
| 5,565,216 A | 10/1996 | Cowsar et al. | |
| 5,902,573 A | 5/1999 | Kapral | |
| 2004/0202725 A1* | 10/2004 | Dascalu | 424/673 |
| 2006/0083706 A1 | 4/2006 | Vic et al. | |
| 2009/0017147 A1* | 1/2009 | Lintner et al. | 424/780 |

FOREIGN PATENT DOCUMENTS

| | | |
|---|---|---|
| JP | 5-25022 A | 2/1993 |
| JP | 5025022 A | 2/1993 |
| WO | 2007099398 A2 | 9/2007 |

OTHER PUBLICATIONS

International Search Report and Written Opinion dated May 15, 2013 from corresponding International Patent Application No. PCT/US2013/028635, 15 pages.
Taiwanese Office Action dated Sep. 17, 2014 for Taiwanese application No. 102110851; pp. 1-11.

* cited by examiner

*Primary Examiner* — David J Blanchard
*Assistant Examiner* — Sarah Chickos
(74) *Attorney, Agent, or Firm* — Ohlandt, Greeley, Ruggiero & Perle, L.L.P.

(57) ABSTRACT

A hair care composition comprising: a crosslinking component comprising an inorganic fluoride; and a conditioning component, wherein the composition has a ratio of crosslinking component to conditioning component in the range of about 10:90 to about 95:5.

10 Claims, 8 Drawing Sheets

HAIR TREATMENT AND REVITALIZING COMPOSITION AND METHODS

CROSS-REFERENCED APPLICATIONS

This application is a Continuation-in-Part of U.S. patent application Ser. No. 13/656,286, filed on Oct. 19, 2012, and claims priority to U.S. Provisional Application No. 61/618,276, filed on Mar. 30, 2012, both of which are incorporated herein by reference thereto in their entireties.

BACKGROUND OF THE DISCLOSURE

1. Field of Disclosure

The present disclosure relates to a hair care composition containing an inorganic fluoride for straightening, smoothing, defrizzing, curling and/or relaxing of hair, and its method of use in a variety of hair care products, e.g., straightener solution, shampoo, conditioner, hair color binding treatment, hair volumizing treatment, combinations thereof, etc.

2. Description of Related Art

During the past few years, there has been a growing trend in the market for semi-permanent curl reduction and change in the configuration of hair with minimum hair damage. These products affect the style configuration of hair with discernible curl reduction and easiness of styling attributes including shine, luster, smoothness, volume reduction, and feel of hair.

Conventional techniques for temporary smoothing and removing curls have been by applying pomades on hair, followed by combing with uncontrollable hot, heated metal combs. These techniques have many serious drawbacks, including scalp burning and hair damage from excessive heat.

Recently, improvements have been made to conventional techniques for smoothing and straightening hair that use controllable flat irons and curling irons. However, the straightening and smoothing effects on hair by these improved methods are only temporary, and total reversion occurs when the person perspires, or is exposed to high humidity, and especially after a single shampoo.

The technique of achieving semi-permanent results of straightening and smoothing was introduced by Brazilian hair stylists using solutions that contained formaldehyde in amounts from 0.2-1.5%, to reduce curl, with longevity of about four to six shampoos. A technique known as "escova progressiva," where the hair was shampooed several times with high pH shampoos of about a pH of 8.5 to swell the hair, and then a "defrizz lotion" containing the formaldehyde and thermal protectors was applied on the hair and processed for 20-30 minutes. The hair was then blow dried and flat ironed. The results from this Brazilian process resulted in temporarily straight, silky, shiny and smooth hair. In order to attain semi-permanent results lasting beyond two to three shampoos, this process required weekly repeat applications.

Recently, several products have entered the market labeled as "keratin treatments." These products have one or more keratin crosslinkers, solubilized keratin protein fractions, emollients, surfactants/emulsifiers, and preservatives. The keratin crosslinkers include monoaldehydes, dialdehydes and polyaldehydes at concentrations of 2% to 10%. The chemical crosslinking and hardening of the proteins with the aldehydes is due to the Maillard reaction. The monoaldehydes are referred to as formol, methanal, or acetaldehyde. These aldehyde-based keratin treatment products have many disadvantages. The major disadvantage with the aldehyde products is their toxicological profiles, creating safety and health concerns.

Formaldehyde, also known as "formol," "methanal," or "methylene glycol," is a suspected carcinogen. Formaldehyde can cause contact dermatitis. Some hair stylists have become ill from repeated exposure to these hair treatments.

Formaldehyde is a colorless, strong-smelling and hazardous chemical that is found in hair smoothing treatments, including the Brazilian Blowout®, owned by Crème De Le Crem Inc. of West Hollywood, Calif. The Brazilian Blowout is regarded as being a more effective and less time-consuming choice than other hair-straightening methods, including conventional relaxers, Japanese thermal processing or keratin based treatments.

In 2011, the Brazilian Blowout has faced warnings and investigations by the Occupational Safety and Health Administration (OSHA) and the U.S. Food and Drug Administration (FDA) for mislabeling its products as "formaldehyde free," when in fact their products contain methylene glycol, a liquid form of the chemical that emits formaldehyde gas when heated. Thus, salon workers and users of the product are exposed to formaldehyde during the entire hair straightening process (typically lasting two hours), especially during some of the key steps of the process, such as blow drying and flat ironing.

Formaldehyde can cause immediate reactions to the immune system, and it is a cancer hazard. It is listed as a human carcinogen in the $12^{th}$ Report on Carcinogens published by the National Toxicology Program. Exposure to formaldehyde can be highly irritating to the eye, nose and throat, which can cause coughing and sneezing. Formaldehyde can cause severe allergic reactions of the skin, eyes, and respiratory tract, and long term exposure to low levels in the air can cause asthma-like respiratory problems and skin irritations such as dermatitis and itching. In women, exposure to formaldehyde can also cause menstrual disorders.

If hair salons do choose to use the hair straightening treatments that contain formaldehyde, they must comply with strict requirements set out in OSHA's formaldehyde standard, which sets a permissible exposure limit for formaldehyde in the workplace at 0.75 parts of formaldehyde per million parts of air (0.75 ppm). Furthermore, the standard requires that employers test the air to find out the level of formaldehyde present in the air when the product is being used.

The difficulty and costs of complying with standards for formaldehyde places a significant burden on salon owners who choose to use hair smoothing products that contain or emit formaldehyde. Due to the health concerns of using hair straightening products that contain formaldehyde, some salons have stopped offering the Brazilian Blowout treatment, at the cost of losing customers.

Products containing more than 0.10% formaldehyde are prohibited in the marketplaces of several countries. Since these products are unstable, they are formulated with a large excess of formaldehyde exceeding the permissible level. At levels of less than 2% formaldehyde, limited crosslinking and polymerization occurs on hair with some level of curl relaxation with shiny and better fiber alignment shown as frizz reduction. The curl reversion is almost quantitative within two or three shampoos, but the cuticular attributes have a few more shampoos of longevity. At higher concentrations of formaldehyde (4-8%), high crosslinking and fast rates of polymerization occur with a discernable curl reduction of hair. Also, at these high levels, there is no need for a waiting period of 72 hours, and hair can be shampooed on the same or next day.

Even though the hair appears shiny and healthy, the formaldehyde polymerization seals the cuticle and traps some of the formula agents into the hair shaft or cortex, making the hair unhealthy. This is due to the water displacement and changes to the melanin, cortical cells, and matrix of hair. Over time, the changes in the cortical cells and microfilaments are irreversible and result in hair damage. Repeat treatments can amplify this damage, which results in fiber failure and hair breakage.

The present inventors have unexpectedly discovered that the application of an inorganic fluoride, such as a sodium fluoride, is a unique non-toxic, non-carcinogenic, product that can be used to straighten, smooth, defrizz or curl hair. It is unexpected since sodium fluoride has never been associated with hair care and nothing found in the literature would suggest to one of ordinary skill in the art the use of such an inorganic fluoride in hair care formulation for the purpose of straightening, smoothing, defrizzing, or curling hair. Moreover, the use of sodium fluoride, as an inorganic salt, in a hair care product ingredient is completely counterintuitive. That is, one would typically avoid the use of inorganic salts generally in hair care formulations, since these salts are known to cause build-up on the hair and many hair cleansing products (e.g., chelating shampoos) are formulated to remove inorganic salts from the hair rather than add such salts to the hair.

SUMMARY

The present disclosure provides a composition to apply to hair that contains fluoride for straightening, smoothing, defrizzing, and/or relaxing hair, and its method of use in a variety of hair care products, e.g., straightener solution, shampoo, conditioner, hair color binding treatment, volumizing treatment, a combination thereof, etc.

A hair care composition comprising: a crosslinking component comprising an inorganic fluoride; and a conditioning component, wherein the composition has a ratio of crosslinking component to conditioning component in the range of about 10:90 to about 95:5, preferably about 75:25.

The inorganic fluoride is present in the crosslinking component in a concentration of between about 0.1 to about 15%. The crosslinking component has a pH range of between about 3.0 to about 8.5, preferably between about 4.5 to about 5.5.

The crosslinking component further comprising at least one additional component selected from the group consisting of: a thickener, a preservative, a humectant, a pH adjuster, soothing agent, emollients, emulsifiers, fragrance and water.

The crosslinking component comprises: the inorganic fluoride having a concentration in the range between about 0.1 to about 15%; the preservative having a concentration in the range between about 0.2 to about 1%; the humectant having a concentration in the range between about 0.1 to about 1%; and the water to bring the concentration up to 100%. The crosslinking component further comprising a pH adjuster to bring the crosslinking component to a pH in the range between about 3.0 to about 8.5.

The inorganic fluoride is at least one selected from the group consisting of: sodium fluoride, potassium fluoride, ammonium fluoride, lithium fluoride, stannous fluoride, aluminum fluoride, zirconium fluoride, nickel fluoride, tin fluoride, ammonium hexafluorophosphate, sodium monofluorophosphate, stannous fluorozirconate, and stannous chlorofluoride.

The preservative is at least one selected from the group consisting of: phenoxyethanol, sorbitol, potassium sorbate, sodium sorbate, methyl paraben, propyl paraben, imidazolidynyl urea, and DMDM hydantoin.

The humectant is at least one selected from the group consisting of: glycerine, propylene glycol, dipropylene glycol, diglycerin, panthenol, sodium PCA, sugar alcohols, lecithin, hydrolyzed wheat proteins, hydrolyzed rice proteins, hydrolyzed keratin proteins, hydrolyzed silk proteins, lipids and polyols.

The thickener is at least one selected from the group consisting of: polysaccharide, cellulose, cellulose, derivatives, natural gums, natural polymers, synthetic polymers and inorganic gel mineral silicates.

The pH adjuster is at least one selected from the group consisting of: phosphoric acid, citric acid, tartaric acid, lactic acid, acetic acid, and bases that include sodium hydroxide, potassium hydroxide, sodium carbonate, ammonium hydroxide, isopropanolamine, and monoethanolamine.

The inorganic fluoride is present in the crosslinking component in a concentration of between about 0.1 to about 3.0%, more preferably between about 0.4 to about 1.25%.

The conditioning component comprises at least one selected from the group consisting of: amodimethicone, cyclomethicone, dimethicone, behentrimonium methosulfate, citrimonium chloride, citrimonium bromide, cocotrimonium methosulfate, olealkonium chloride, phenyltrimethicone, pantethine, panthenylethylether, silicone quaternium, gelatin, keratin amino acids, and polyquaternium.

A method for treating hair comprising: applying a premixed composition comprising (a) a crosslinking component comprising an inorganic fluoride and (b) a conditioning component to a user's hair, wherein the hair is straightened, smoothed, defrizzed or curled and wherein the premixed composition has a ratio of crosslinking component to conditioning component in the range of about 10:90 to about 95:5.

The fluoride is preferably a salt with an alkali metal (such as sodium fluoride, potassium fluoride, or lithium fluoride), or as ammonium fluoride, stannous fluoride, or with hexafluorophosphate.

The compositions of the present disclosure can be applied to any type of hair, with excellent results in hair straightening, smoothing, defrizzing, and/or relaxing.

The hair care compositions of the present disclosure are formaldehyde-free, even when heated by blow drying or flat ironing.

DETAILED DESCRIPTION OF THE PREFERRED EMBODIMENT

Figure 1:
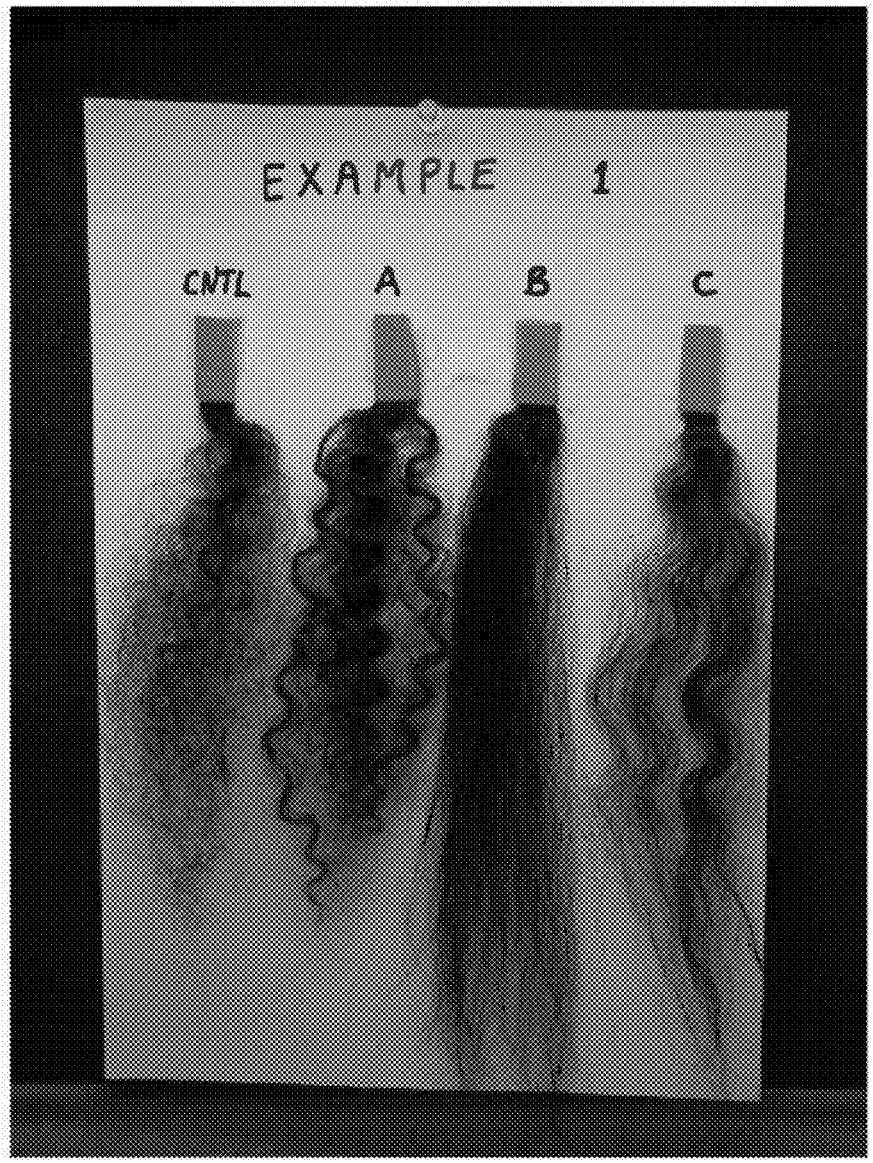
FIG. 1 shows the results for Example 1, with a sample of a control (untreated hair) and three samples of normal hair treated with 1% sodium fluoride at pH 4.8, for very curly normal hair.

The present inventors have unexpectedly discovered that due to the small molecular size of the fluoride, and its affinity for multiple cross-linking sites, the fluoride can produce cross-linkage in hair and cause temporary or permanent restructuring of the hair; i.e. causes straightening, smoothing, defrizzing and/or curling of the hair fiber.

More particularly, the use of sodium fluoride can be used in hair products for straightening, smoothing, defrizzing and/or curling. Sodium fluoride has excellent water solubility.

Unexpectedly, the present inventors have discovered that the fluoride can be used to crosslink other molecules to the hair to provide long lasting conditioning or volume to the hair. It can also be used to bind hair dye molecules in the hair for longer lasting coloring of the hair.

Sodium fluoride is an alternative to conventional hair products using formaldehyde.

Our data show that compositions for hair treatment having about 0.1 to about 15%, preferably about 0.1 to about 3.0%, and more preferably about 0.60 to about 1.25% sodium fluoride at pH 4.8, along with a polysaccharide thickener (such as AMIGEL®) has a perceptible effect on curl reduction, and that smoothening or better alignment of hair fibers is observed for all normal and porous hair types.

The compositions of the present disclosure include:

| Composition | |
|---|---|
| Inorganic fluoride compound M-Fluoride | 0.1-15% |
| Preservative | 0.2-1% |
| Humectant | 0.1-1% |
| pH adjuster | to pH 3.0-8.5 |

M = Sodium, Potassium, Ammonium, Lithium, Stannous, Hexafluorophosphate

The treatment composition below was used for several performance examples:

| Composition | w/w |
|---|---|
| Sodium fluoride (protein crosslinker) | 1-2 |
| Phenoxyethanol (preservative) | 0.2% |
| Glycerine (humectant) | 0.5% |

-continued

| Composition | w/w |
|---|---|
| AMIGEL ® (polysaccharide thickener) | 0.6% |
| Phosphoric acid (QS) | to pH 4.8 |
| Water (QS) | to 100% |

FIGS. 1 to 7 show the effects of a sodium fluoride composition on several hair types, normal and porous hair including 20 volume color treated and bleached hair. The results from Examples 1 to 7 below are shown in FIGS. 1 to 7, respectively.

In each of the following examples, the hair was treated as follows: The hair was shampooed and blotted dry. The hair was combed and the treatment composition was applied on the hair for 35 minutes at room temperature with a brush and then it was treated as in the directions below for each of Examples 1 to 7.

All samples marked "CNTL" are untreated hair.

For all hair samples marked "A", the treatment composition was applied for 35 minutes and then the hair was rinsed with tap water. The hair was air-dried naturally.

For all hair samples marked "B", the treatment composition was applied for 35 minutes and then the hair was rinsed with tap water. The hair was blow dried to about 90% and then flat ironed at 430° F. The hair was then rinsed with tap water.

For all hair samples marked "C", the treatment composition was applied for 35 minutes and then the hair blow dried at a medium setting to about 90%, and then flat ironed at 430° F. The hair was then rinsed with tap water, and the hair was air-dried naturally.

Example 1

Normal Hair

For Example 1, shown in FIG. 1, a composition of the present disclosure containing 1% sodium fluoride at pH 4.8 was applied to very curly normal hair.

Example 2

20 Volume Color Treated Hair

Figure 2:
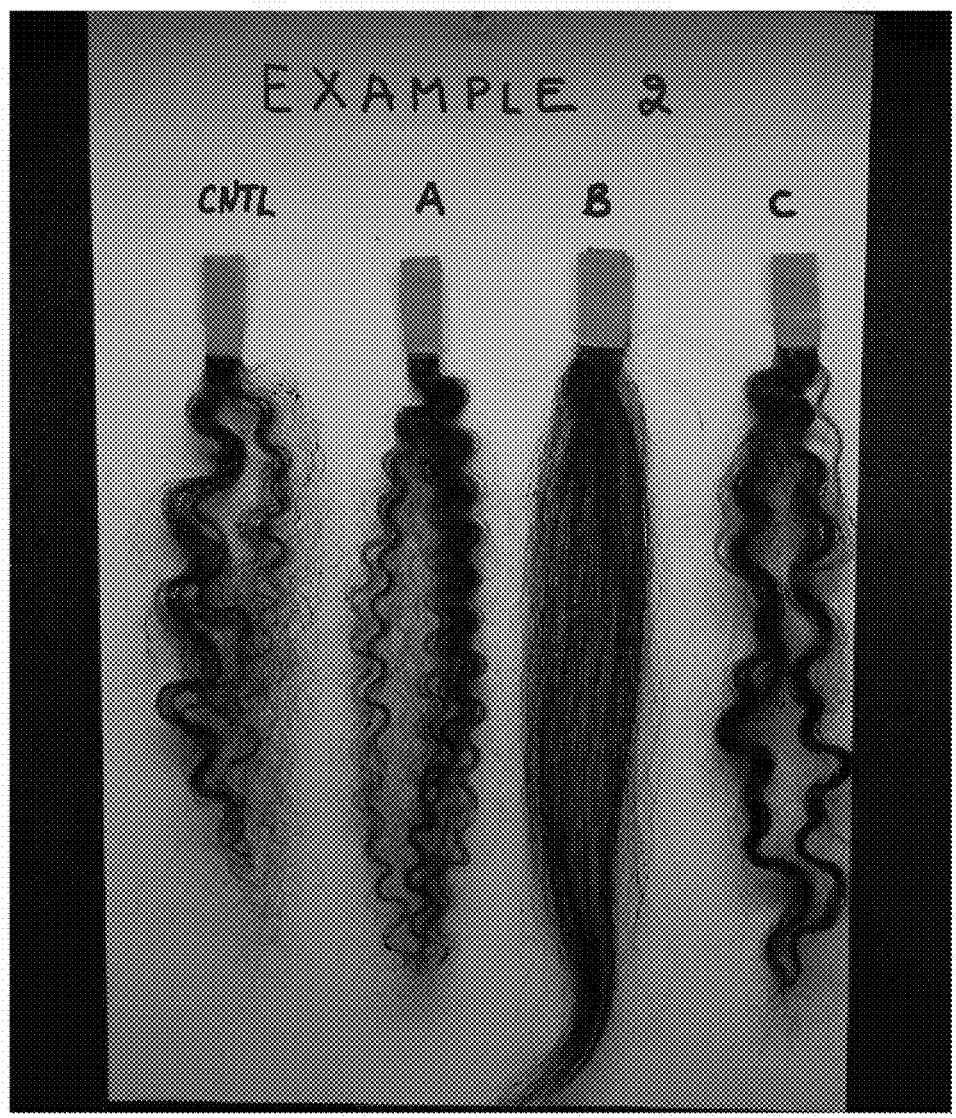
FIG. 2 shows the results for Example 2, with a sample of a control (untreated hair) and three samples of 20 volume color treated hair treated with 1% sodium fluoride at pH 4.8, for very curly 20 volume hair.

For Example 2, shown in FIG. 2, a composition of the present disclosure containing 1% sodium fluoride at pH 4.8 was applied to very curly 20 volume hair.

Example 3

40 Volume Bleached Hair

Figure 3:
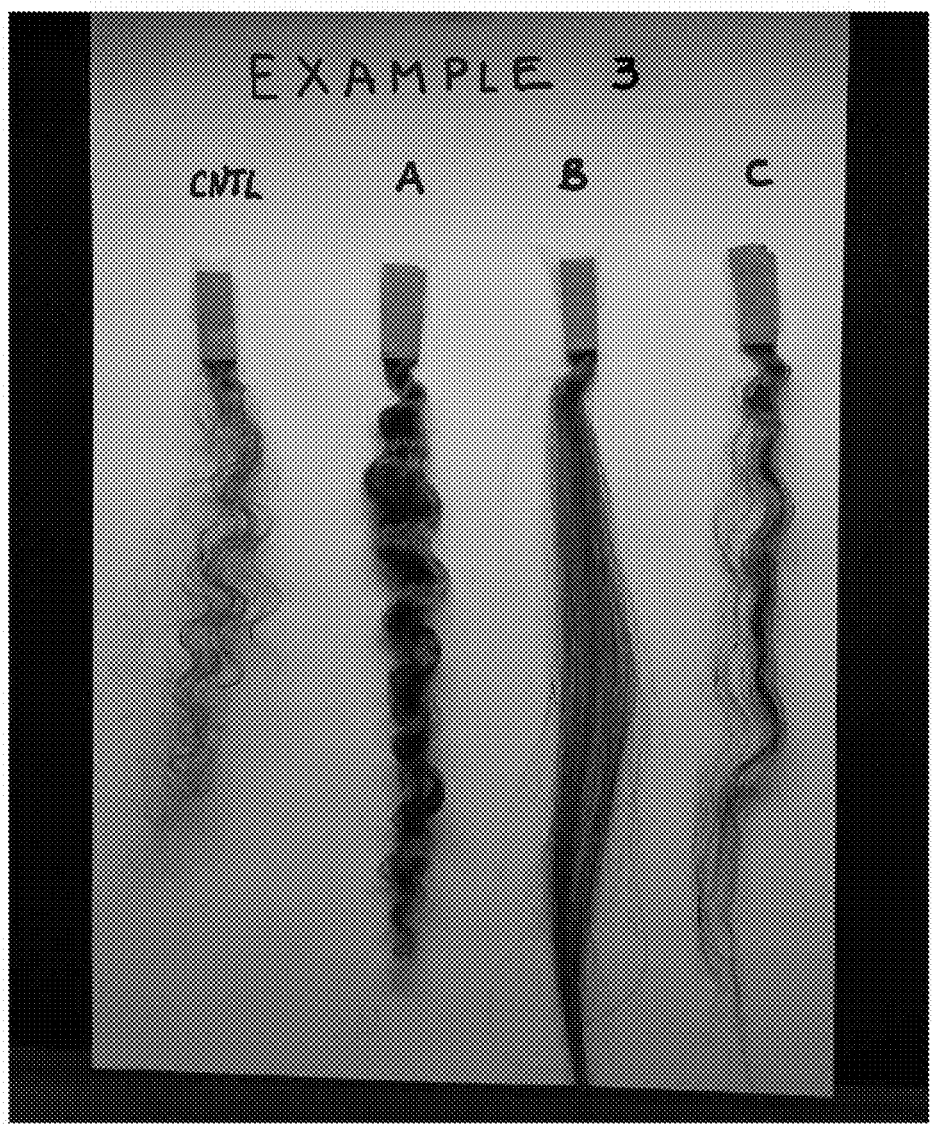
FIG. 3 shows the results for Example 3, with a sample of a control (untreated hair) and three samples of 40 volume bleached hair treated with 1% sodium fluoride at pH 4.8, for very curly 40 volume bleached hair.

For Example 3, shown in FIG. 3, a composition of the present disclosure containing 1% sodium fluoride at ~pH 4.8 was applied to very curly 40 volume bleached hair.

Example 4

20 Volume Hair

Figure 4:
FIG. 4 shows the results for Example 4, with a sample of a control (untreated hair) and three samples of wavy 20 volume hair treated with 1% sodium fluoride at pH 4.8, for wavy 20 volume hair.

For Example 4, shown in FIG. 4, a composition of the present disclosure containing 1% sodium fluoride at ~pH 4.8 was applied to wavy 20 volume hair.

Example 5

Normal Hair

Figure 5:
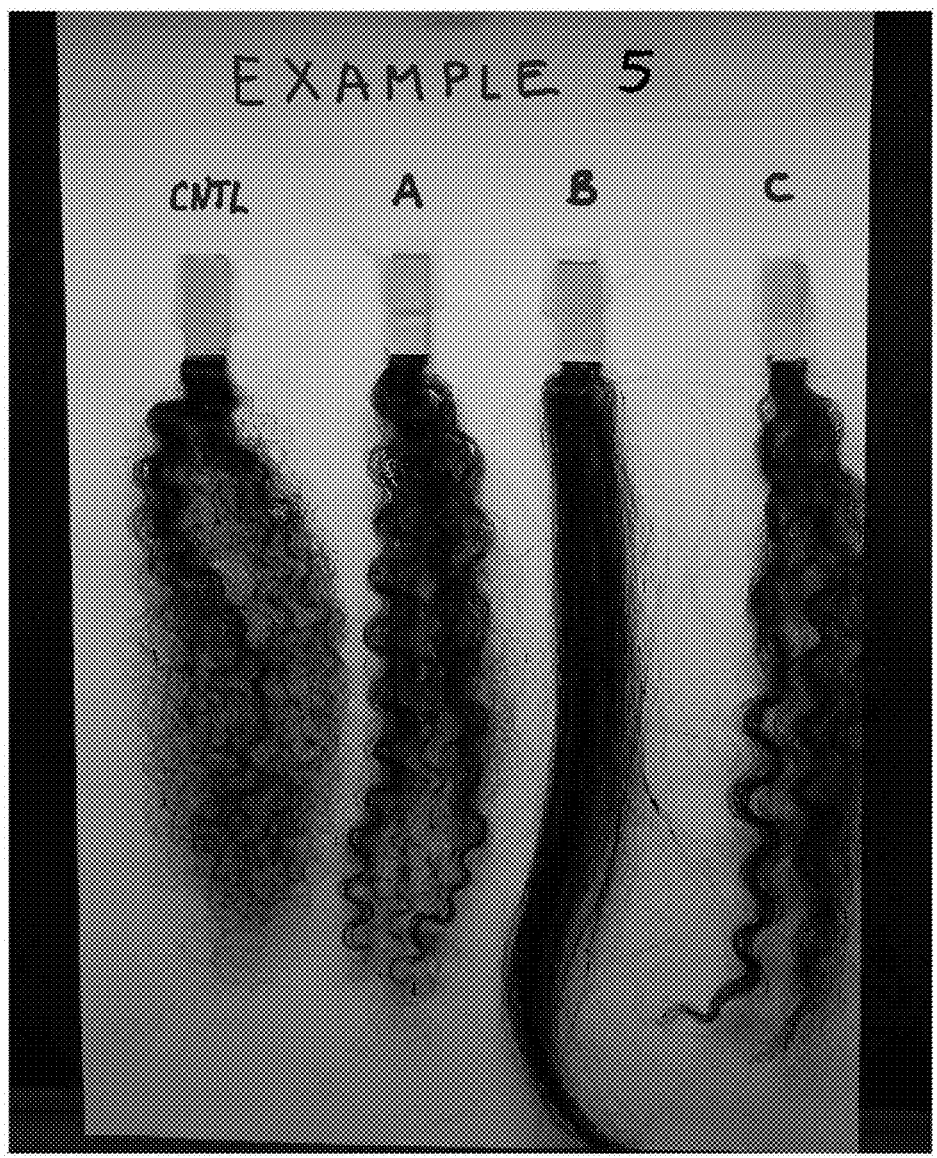
FIG. 5 shows the results for Example 5, with a sample of a control (untreated hair) and three samples of normal hair treated with 2% sodium fluoride at pH 4.8, for very curly normal hair.

For Example 5, shown in FIG. 5, a composition of the present disclosure containing 2% sodium fluoride at a pH of approximately 4.8 was applied to very curly normal hair.

Example 6

40 Volume Bleached Hair

Figure 6:
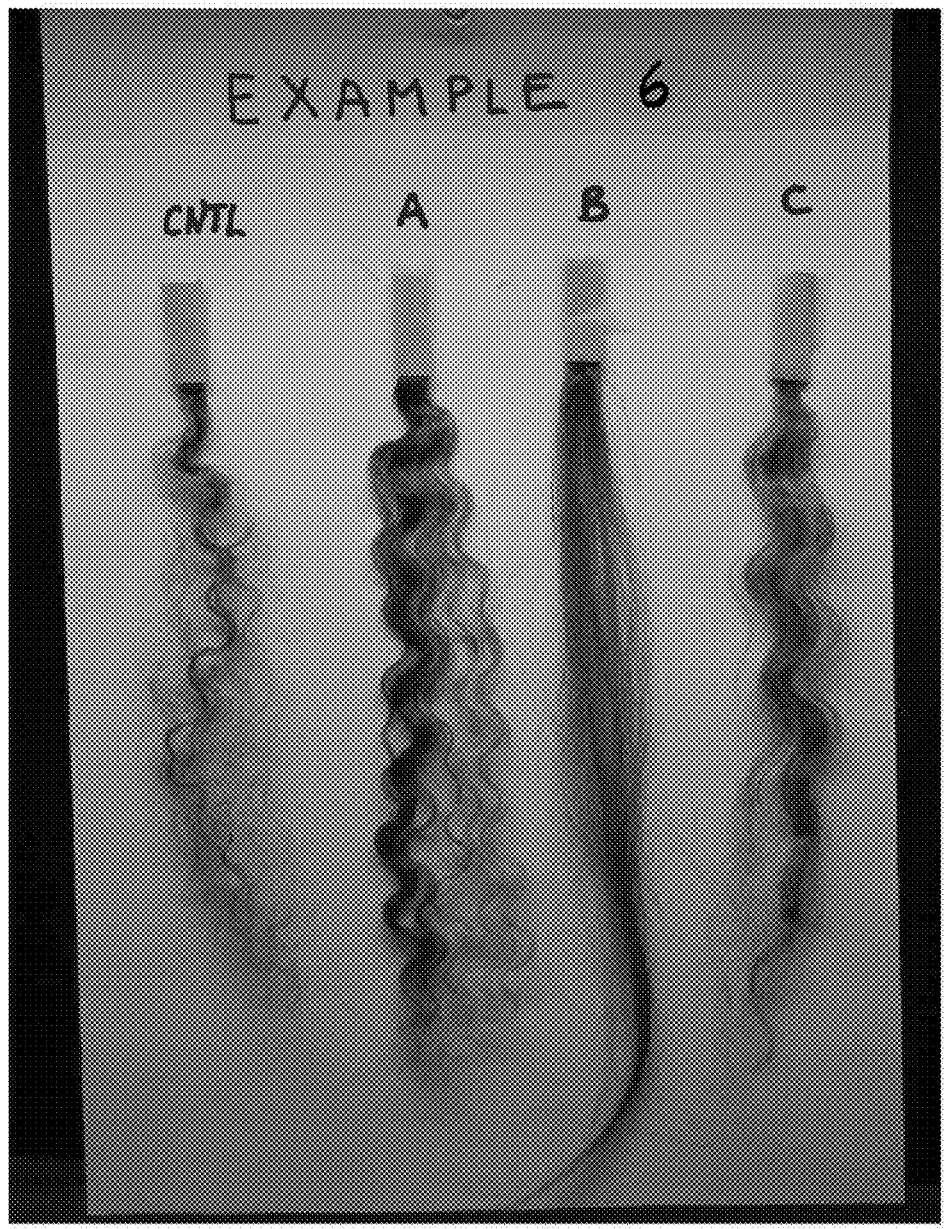
FIG. 6 shows the results for Example 6, with a sample of a control (untreated hair) and three samples of 40 volume bleached hair treated with 1.5% sodium fluoride at pH 4.8, for 40 Volume bleached hair.
Figure 7:
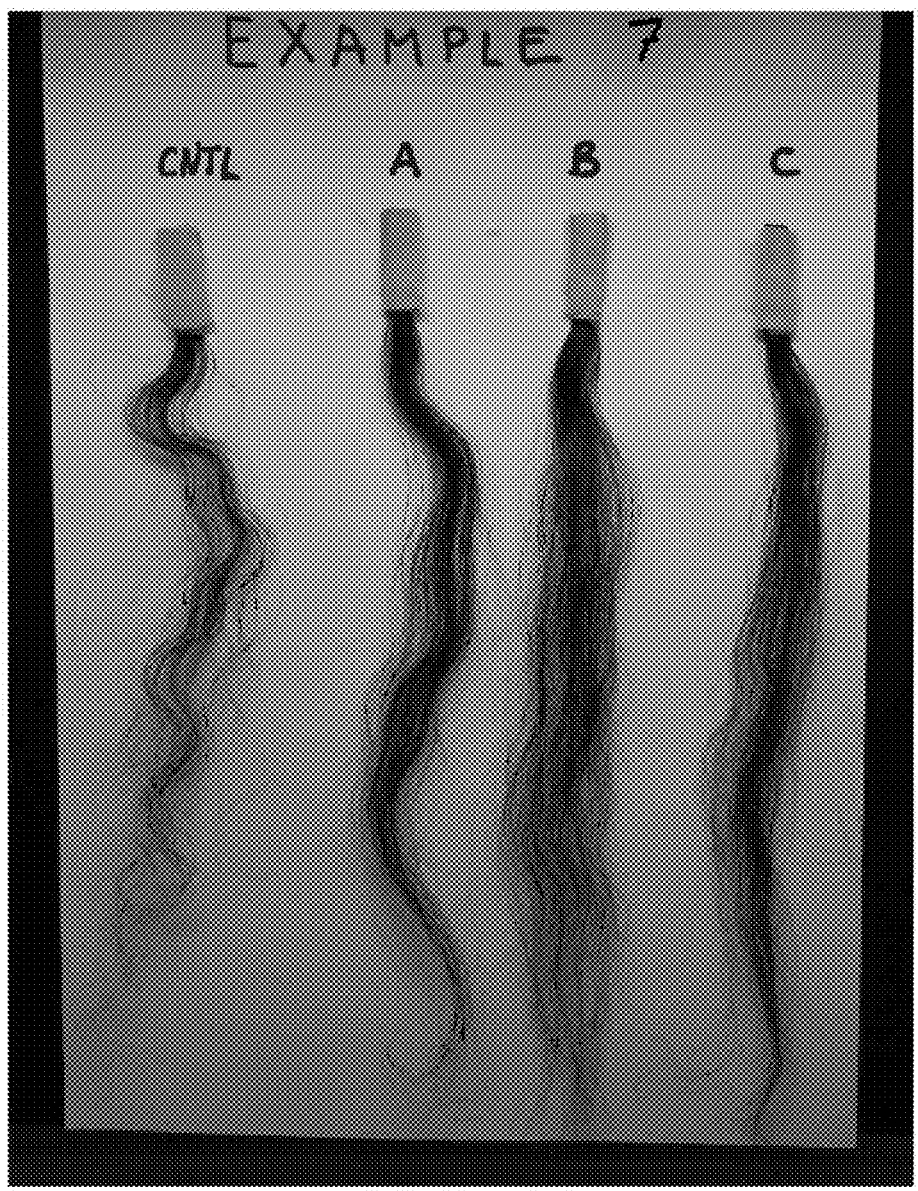
FIG. 7 shows the results for Example 7, with a sample of a control (untreated hair) and three samples treated at pH 4.8, where A=1.0% sodium fluoride, B=1.5% sodium fluoride, and C=2.0% sodium fluoride.
Figure 8:
FIG. 8 shows the results for Example 8, with a sample of a control (untreated hair) and two samples of normal curly hair treated with Brazilian Blow Out (O=Original Formula 7-8% formaldehyde and Z=Zero Formaldehyde Formula).

For Example 6, show in FIG. 6, a composition of the present disclosure containing 1.5% sodium fluoride at a pH of approximately 4.8 was applied to 40 volume bleached hair.

Example 7

Normal Curly Hair

For Example 7, samples A, B, and C were treated as follows: The treatment composition was applied to the hair for 35 minutes. The hair was blow dried at medium heat setting to about 90% dry, and then flat-ironed at 430° F. The hair was then rinsed with tap water, and the hair was air dried naturally.

A=1.0% sodium fluoride at a pH of approximately 4.8
B=1.5% sodium fluoride at a pH of approximately 4.8
C=2.0% sodium fluoride at a pH of approximately 4.8

Example 8

Brazilian Blow Out on Normal Curly Hair

Samples O and Z were treated as follows: The treatment composition was applied to the hair for 35 minutes, and then the hair was blow dried at a medium heat setting to about 90% dry. The hair was then flat-ironed at 430° F., and then was rinsed with tap water. The hair was then air dried naturally.

O=Brazilian Blowout Original Formula 7-8% Formaldehyde content
Z=Brazilian Blowout Zero Formaldehyde Formula As used in this application, the word "about" for dimensions, weights, and other measures, means a range that is ±10% of the stated value, more preferably ±5% of the stated value, and most preferably ±2% of the stated value, including all sub ranges there between.

In practice of the present disclosure one or more other extended cosmetic compositions can be included for their generally acceptable recognized purposes. These can include soothing agents, such as aloe or allantoin gelatin; auxiliary emollients, such as squalene, mineral oil, argan oil, coconut oil, jojoba oil, walnut oil or liquid silicones; fatty alcohol based thickeners, such as cetyl alcohol, cetearyl alcohol, or stearic acid; low to no foaming cationic, nonionic or amphoteric emulsifiers; or preservatives, such as phenoxyethanol, sorbitol, potassium sorbate, sodium sorbate, methyl paraben, propyl paraben, Imidazolidynyl urea, or DMDM hydantoin.

The composition may also contain a fragrance to neutralize any malodors of the composition.

Cream Based Composition 1 (Leave On or Rinse Off)

|  | (W/W %) |
|---|---|
| Water | 70 |
| Methyl paraben | 0.15 |
| Ethyl paraben | 0.02 |
| Isopropyl Palmitate | 0.61 |
| Petrolatum | 2.45 |
| Glyceryl Stearate | 2.04 |
| Cetearyl Alcohol | 2.04 |
| Cyclopentasiloxane | 1.02 |
| Fragrance | 0.20 |
| Phenoxyethanol | 0.50 |
| Polyquaternium-37 | 1.23 |
| Sodium Fluoride | 0.5-8 |
| pH adjustor - | QS to pH |
| Water | QS to 100% |

Cream Based Composition 2 (Rinse Off)

|  | (W/W %) |
|---|---|
| Water | 60 |
| Cetyl Alcohol | 3.50 |
| Stearyl Alcohol | 3.00 |
| Dicetyldimonium Chloride | 2.00 |
| Propylene Glycol | 0.10 |
| Polyquaternium-7 | 2.00 |
| Stearyl Alcohol (and) Ceteareth-20 | 2.00 |
| Cyclopentasiloxane | 1.30 |
| Amodimethicone | 1.00 |
| Hydrolyzed Keratin | 1.00 |
| Stearamidopropyl Dimethylamine | 0.50 |
| Fragrance | 0.20 |
| Aminopropyl Phenyl Trimethicone | 0.20 |
| Glycerin | 0.50 |
| Methylparaben | 0.10 |
| Phenoxyethanol | 0.50 |
| Sodium Fluoride | 0.5-8 |
| pH adjustor - | QS to pH |
| Water | QS to 100% |

Cream Based Composition 3 (Leave On or Rinse Off)

|  | (W/W %) |
|---|---|
| Water | 70 |
| Cetearyl Alcohol (and) Ceteareth-20 | 1.80 |
| Hydrolyzed Keratin | 2.00 |
| Amodimethicone | 1.00 |
| Hydrolyzed Keratin | 2.00 |
| Cyclopentasiloxane (and) Dimethicone | 0.50 |
| Cetrimonium Chloride | 0.50 |
| Fragrance/Parfum | 0.20 |
| Hydrolyzed Collagen | 0.20 |
| Propylene Glycol | 0.10 |
| Glycerine | 0.20 |
| Methylparaben | 0.10 |
| (Wheat) Germ Oil | 0.001 |
| Argania Spinosa Kernel Oil | 0.001 |
| Sodium Fluoride | 0.5-8 |
| pH adjustor - | QS to pH |
| Water | QS to 100% |

Gel Based Composition 3 (Leave On or Rinse Off)

|  | (W/W %) |
|---|---|
| Water | 70 |
| Polyquaternium-7 | 4.00 |
| Silkworm Extract | 3.00 |
| Hydrolyzed Keratin | 3.00 |

|  | (W/W %) |
|---|---|
| Glycerin | 2.00 |
| Cetrimonium Chloride | 0.80 |
| Guar Hydroxypropyltrimonium Chloride | 0.60 |
| Phenoxyethanol | 0.50 |
| Panthenol | 0.50 |
| Sodium Fluoride | 0.5-8 |
| pH adjustor - | QS to pH |
| Water | QS to 100% |

Non Ionic Surfactant Smoothing Shampoo

|  | (W/W %) |
|---|---|
| Water | 75 |
| Non ionic Surfactants | 5-15 |
| Foam Boosters | 0.5-10 |
| Opacifier | 0.50-3 |
| Fragrance (Parfum) | 0.20-0.90 |
| Anionic Surfactant/Fatty alcohol | 0.15-2 |
| Fatty Alcohol | 0.2-0.5 |
| Sodium Fluoride | 0.01-2 |
| Preservative | 0.10-0.25 |
| Thickener | 0.05-3 |
| Citric Acid | 0.10-0.5 |
| Chelating Agent | 0.08-0.30 |
| Sodium Citrate (and) Water (Aqua) | QS to pH 4.5-5.5 |
| Water | QS to 100% |

Anionic Surfactant Smoothing Shampoo

|  | (W/W %) |
|---|---|
| Water | 75 |
| Anionic Surfactants | 5-15 |
| Foam Boosters | 0.5-10 |
| Opacifier | .50-3 |
| Fragrance (Parfum) | 0.20-0.90 |
| Anionic Surfactant/Fatty | 0.2-0.5 |
| Sodium Fluoride | 0.01-2 |
| Preservative | 0.10-0.25 |
| Thickener | 0.05-3 |
| Citric Acid | 0.10-0.5 |
| Chelating Agent | 0.08-0.30 |
| Sodium Citrate (and) Water (Aqua) | QS to pH 4.5-5.5 |
| Sodium Chloride | QS to Viscosity 6,000-9,000 cps |
| Water | QS to 100% |

TABLE I

PERFORMANCE EFFECTS OF 1% NaF Versus pH ON CURLY/FRIZZY HAIR
(NORMAL CURLY, COLOR TREATED AND BLEACHED HAIR TYPE)

COMPOSITION I

| NaF | 1.00% |
|---|---|
| Amigel Thickener | 0.60% |
| Glycerol | 0.50% |
| Phenoxyethanol | 0.20% |
| pH Adjustor | pH adjustment only |
| QS DI Water | QS. |

Process A: The hair swatches are shampooed with a Clarifying shampoo, towel blot and dried at medium heat with blow dryer. The composition I product was applied liberally to the hair with a tint brush and processed for 35 minutes. The excess product was towel blotted and the hair is dried to about 95% with a blow dryer at low heat followed with flat ironing @ 430° F. using 7-8 passes. The hair was rinsed after 48 hours. The performance % Curl Reduction, Shine and Smoothness was evaluated.

| PERFORMANCE | pH | Lo (cm) | Ls (cm) | Lt (cm) | % Curl Reduction | Shine | Smoothness |
|---|---|---|---|---|---|---|---|
| NORMAL CURLY HAIR | 3.51 | 18.2 | 27.1 | 22.2 | 44.94% | +++ | ++++ |
| ($H_2PO_4$) | 3.99 | 18.2 | 27.3 | 22.3 | 45.05% | +++ | ++ |
|  | 4.5 | 18.2 | 26.8 | 25.3 | 82.56% | +++ | ++++ |
|  | 5.02 | 18.2 | 27.2 | 19.8 | 17.78% | ++ | ++ |
|  | 5.95 | 18.2 | 25.4 | 19.6 | 19.44% | ++ | ++ |
|  | 6.93 | 18.2 | 27.9 | 20.3 | 21.65% | +++ | ++ |
|  | 7.99 | 18.2 | 27.2 | 22.1 | 36.79% | +++ | ++++ |
| NORMAL CURLY HAIR | 3.82 | 16.6 | 23.3 | 19.1 | 37.31% | + | +++ |
| (CITRIC ACID) | 4.1 | 16.6 | 24.6 | 20.2 | 45.00% | ++ | ++++ |
|  | 4.51 | 16.6 | 25.3 | 18.7 | 24.14% | +++ | +++ |
|  | 5.03 | 16.6 | 26.3 | 17.6 | 10.31% | +++ | ++ |
|  | 6.02 | 16.6 | 24.7 | 19.1 | 30.86% | +++ | ++++ |
|  | 7.03 | 16.6 | 24.1 | 18.2 | 21.33% | +++ | +++ |
|  | 8.06 | 16.6 | 25.2 | 18.3 | 32.69% | ++++ | ++ |
| 20 VOL COLOR | 3.01 | 20.0 | 26.00 | 22.50 | 41.66% | +++ | +++ |
| TREATED HAIR | 3.99 | 20.0 | 25.00 | 21.50 | 30.00% | +++ | +++ |
| (H2PO4) | 4.49 | 19.0 | 25.50 | 22.00 | 46.15% | ++++ | ++++ |
|  | 5.02 | 19.0 | 26.00 | 22.00 | 42.85% | ++++ | +++ |
|  | 6.93 | 18.0 | 24.00 | 22.50 | 75% | +++ | +++ |
|  | 7.99 | 18.0 | 26.00 | 23.00 | 62.50% | +++ | ++++ |
| 2X 40 VOL BLEACHED | 3.01 | 20.0 | 26.00 | 24.00 | 66.66% | ++ | + |
| HAIR | 3.99 | 22.0 | 29.00 | 23.00 | 14.28% | ++ | ++ |
| (H2PO4) | 4.49 | 21.0 | 27.00 | 25.50 | 75.00% | +++ | ++++ |
|  | 5.02 | 21.0 | 25.00 | 22.00 | 25.00% | ++ | ++++ |
|  | 6.93 | 20.0 | 25.50 | 23.00 | 54.55% | +++ | +++ |
|  | 7.99 | 21.0 | 27.00 | 24.00 | 50.00% | +++ | ++++ |

TABLE I-continued

Process B: The hair swatches are shampooed with Clarifying shampoo, towel blot and dried at medium heat with blow dryer. The composition I product was applied liberally to the hair with a tint brush and processed for 35 minutes. The excess product was towel blotted and hair was blow dried straight at high heat setting using a brush. The hair was rinsed after 48 hrs. The performance % Curl Reduction, Shine and Smoothness was evaluated.

| PERFORMANCE | pH | Lo (cm) | Ls (cm) | Lt (cm) | % Curl Reduction | Shine | Smoothness |
|---|---|---|---|---|---|---|---|
| NORMAL CURLY HAIR | 3.51 | 16.3 | 27.3 | 21.2 | 44.55% | +++ | +++ |
| ($H_2PO_4$) | 3.99 | 16.3 | 26.1 | 18.3 | 20.41% | +++ | +++ |
| | 4.49 | 16.3 | 26.7 | 18.9 | 25.00% | ++++ | ++++ |
| | 5.02 | 16.3 | 23.6 | 17.5 | 16.44% | ++ | ++ |
| | 5.95 | 16.3 | 26.8 | 18.2 | 18.10% | ++ | ++ |
| | 6.93 | 16.3 | 27.1 | 19.2 | 26.85% | ++ | +++ |
| | 7.99 | 16.3 | 27.5 | 20.3 | 35.71% | +++ | ++++ |
| NORMAL CURLY HAIR | 3.82 | 13.8 | 26.8 | 17 | 24.62% | +++ | ++ |
| (CITRIC ACID) | 4.1 | 13.8 | 23.9 | 14.9 | 10.89% | ++++ | ++++ |
| | 4.51 | 13.8 | 23.7 | 15.4 | 16.16% | ++++ | ++++ |
| | 5.03 | 17.5 | 26.5 | 18.7 | 13.33% | ++ | ++ |
| | 6.02 | 13.8 | 22.6 | 15.8 | 22.73% | ++ | ++ |
| | 7.03 | 13.8 | 23.7 | 14.2 | 4.04% | +++ | +++ |
| | 8.06 | 13.8 | 24.2 | 17.4 | 34.62% | +++ | +++ |
| 20 VOL COLOR | 3.01 | 14.0 | 22.0 | 18.5 | 56.25% | ++ | ++ |
| TREATED HAIR | 3.99 | 17.5 | 24.0 | 20.5 | 46.15% | ++ | ++ |
| (H2PO4) | 4.49 | 18.5 | 24.0 | 20.0 | 27.27% | ++++ | ++++ |
| | 5.02 | 15.0 | 24.0 | 19.0 | 44.44% | +++ | +++ |
| | 6.93 | 13.0 | 23.0 | 18.5 | 55.00% | ++ | ++ |
| | 7.99 | 16.0 | 24.0 | 19.5 | 43.75% | +++ | + |
| 2X 40 VOL BLEACHED | 3.01 | 17.5 | 24.0 | 19.5 | 30.77% | ++ | + |
| HAIR | 3.99 | 18.0 | 25.0 | 19.5 | 21.43% | ++ | +++ |
| (H2PO4) | 4.49 | 16.0 | 24.5 | 20.0 | 47.06% | +++ | ++++ |
| | 5.02 | 16.0 | 24.0 | 19.0 | 37.50% | ++ | ++ |
| | 6.93 | 19.0 | 25.0 | 22.5 | 58.33% | ++ | +++ |
| | 7.99 | 17.0 | 25.0 | 20.0 | 37.50% | +++ | ++ |

Process C: The hair swatches are shampooed with Clarifying shampoo, towel blot and dried at medium heat with blow dryer. The composition I product was applied liberally to the hair with a brush and processed for 35 minutes. The excess product was towel blotted and air dried from the hair. The hair was rinsed after 48 hrs. The performance % Curl Reduction, Shine and Smoothness was evaluated.

| PERFORMANCE | pH | Lo (cm) | Ls (cm) | Lt (cm) | % Curl Reduction | Shine | Smoothness |
|---|---|---|---|---|---|---|---|
| NORMAL CURLY HAIR | 3.51 | 17.5 | 26.2 | 20.5 | 34.48% | + | + |
| ($H_2PO_4$) | 3.99 | 13.8 | 24.5 | 17.5 | 34.58% | + | + |
| | 4.49 | 17.5 | 24.3 | 18.4 | 13.24% | + | +++ |
| | 5.02 | 13.8 | 24 | 16.7 | 28.43% | + | ++ |
| | 5.95 | 17.5 | 24.5 | 19.2 | 24.29% | ++ | + |
| | 6.93 | 17.5 | 24.3 | 18.5 | 14.71% | +++ | ++ |
| | 7.99 | 17.5 | 24.3 | 18.4 | 13.24% | ++ | + |
| NORMAL CURLY HAIR | 3.82 | 17.5 | 25.8 | 19.4 | 22.89% | + | ++ |
| (CITRIC ACID) | 4.1 | 17.5 | 25.6 | 19 | 18.52% | + | + |
| | 4.51 | 17.5 | 26.2 | 17.9 | 4.60% | +++ | +++ |
| | 5.03 | 17.5 | 25.1 | 17.8 | 3.95% | + | + |
| | 6.02 | 14.8 | 25 | 17.8 | 29.41% | + | + |
| | 7.03 | 14.8 | 25.6 | 16.8 | 18.52% | +++ | +++ |
| | 8.06 | 14.8 | 26.8 | 18.6 | 31.67% | ++ | ++ |
| 20 VOL COLOR | 3.01 | 15.0 | 25.0 | 18.0 | 30.00% | ++ | ++ |
| TREATED HAIR | 3.99 | 14.0 | 23.0 | 16.0 | 22.22% | +++ | +++ |
| (H2PO4) | 4.49 | 18.5 | 25.0 | 19.0 | 7.69% | +++ | +++ |
| | 5.02 | 18.0 | 25.0 | 18.5 | 7.14% | ++ | ++ |
| | 6.93 | 18.0 | 25.0 | 18.0 | 0.00% | +++ | ++ |
| | 7.99 | 13.0 | 24.0 | 16.0 | 27.27% | +++ | +++ |
| 2X 40 VOL BLEACHED | 3.01 | 17.0 | 25.0 | 20.0 | 37.50% | + | + |
| HAIR (H2PO4) | 3.99 | 16.0 | 25.0 | 18.5 | 27.78% | +++ | +++ |
| | 4.49 | 16.0 | 24.0 | 18.0 | 25.00% | +++ | ++++ |
| | 5.02 | 18.0 | 26.0 | 19.0 | 12.50% | +++ | ++++ |
| | 6.93 | 16.0 | 24.0 | 18.5 | 31% | ++ | ++ |
| | 7.99 | 21.0 | 28.0 | 21.0 | 0.00% | +++ | +++ |

Process D: The hair swatches are shampooed with Clarifying shampoo, towel blot and dried at medium heat with blow dryer. The Composition I was applied liberally to the hair with a brush and processed for 35 minutes. The hair was rinsed with luke warm water. The hair is dried to about 95% with a blow dryer at low heat followed with flat ironing @ 430° F. using 7-8 passes. The hair was rinsed after 48 hours. The performance % Curl Reduction, Shine and Smoothness was evaluated.

| PERFORMANCE | pH | Lo (cm) | Ls (cm) | Lt (cm) | % Curl Reduction | Shine | Smoothness |
|---|---|---|---|---|---|---|---|
| NORMAL CURLY HAIR | 3.51 | 15.3 | 23.2 | 16.5 | 15.19% | +++ | ++++ |
| ($H_2PO_4$) | 3.99 | 15.3 | 25.4 | 17.7 | 23.76% | +++ | ++++ |
| | 4.49 | 15.3 | 26.1 | 19.7 | 40.74% | ++++ | ++++ |

TABLE I-continued

| | pH | Lo | Ls | Lt | % Curl Reduction | Shine | Smoothness |
|---|---|---|---|---|---|---|---|
| | 5.02 | 15.3 | 22.8 | 17.3 | 26.67% | ++ | +++ |
| | 5.95 | 15.3 | 23.8 | 17.5 | 25.88% | +++ | +++ |
| | 6.93 | 15.3 | 23.6 | 19.3 | 48.19% | ++++ | ++++ |
| | 7.99 | 15.3 | 22.7 | 16.8 | 20.27% | +++ | ++++ |
| NORMAL CURLY HAIR (CITRIC ACID) | 3.82 | 14.8 | 26.3 | 16.2 | 12.17% | ++ | ++ |
| | 4.1 | 14.8 | 24.2 | 18.7 | 41.49% | +++ | +++ |
| | 4.51 | 14.8 | 25 | 17.7 | 28.43% | +++ | +++ |
| | 5.03 | 14.8 | 24.8 | 17.2 | 24.00% | ++ | ++ |
| | 6.02 | 14.8 | 25.8 | 18.5 | 33.64% | + | + |
| | 7.03 | 14.8 | 26 | 18.2 | 30.36% | ++ | ++ |
| | 8.06 | 14.8 | 25.2 | 17.4 | 25.00% | ++ | ++ |
| 20 VOL COLOR TREATED HAIR (H2PO4) | 3.01 | 16.0 | 27.0 | 20.0 | 36.36% | ++ | ++ |
| | 3.99 | 14.0 | 24.0 | 19.0 | 50.00% | + | ++ |
| | 4.49 | 17.0 | 24.0 | 20.0 | 42.86% | +++ | ++++ |
| | 5.02 | 14.0 | 25.0 | 19.0 | 45.45% | ++ | ++ |
| | 6.93 | 15.0 | 24.0 | 20.0 | 55.56% | ++ | +++ |
| | 7.99 | 17.0 | 25.0 | 21.0 | 50.00% | +++ | ++ |
| 2X 40 VOL BLEACHED HAIR (H2PO4) | 3.01 | 19.0 | 26.0 | 24.5 | 78.57% | + | + |
| | 3.99 | 21.0 | 26.0 | 22.5 | 30.00% | +++ | ++++ |
| | 4.49 | 19.0 | 24.0 | 22.0 | 60.00% | +++ | ++++ |
| | 5.02 | 19.0 | 24.0 | 22.0 | 60.00% | ++ | ++ |
| | 6.93 | 21.0 | 27.0 | 24.0 | 50% | ++ | ++ |
| | 7.99 | 19.0 | 24.5 | 22.0 | 54.55% | +++ | +++ |

% Curl Reduction Evaluation:
L0 = Initial Length of curly hair
LS = Length of hair @ 100% Curl reduction
LT = Length of treated Curly hair
% Curl reduction = Lt − Lo × 100/Ls − L0
Shine and Smoothness Evaluation:
Grading

| | |
|---|---|
| 0% | ± |
| 0-20% | + |
| 20-40% | ++ |
| 40-60% | +++ |
| 60-80% | ++++ |
| 80-100% | +++++ |

The tabulated data of Table I above shows that the overall performance of curl reduction, shine and smoothness on hair depends on the pH of Composition I and method of application. The performance appears to be dependent on the pH and independent of the type of pH adjustor. The optimum performance of Composition I pH range on Normal, Color treated and Bleached hair, appears to be between 4-5. Also, the performance effects are dependent on the method of application of composition I. Application methods A and D are preferable over methods B and C. Both methods A and D have high heat flat ironing greater than 400° F. with Composition I or rinsed off the hair. Curl reduction, increase in Smoothness and Shine of 40-80% have been observed on Normal, Color treated and Bleached hair.

TABLE IA pH PERFORMANCE EFFECTS OF 1% NaF ON VERY CURLY/FRIZZY HAIR
(NORMAL, COLOR TREATED AND BLEACHED HAIR TYPE)

COMPOSITION I

| | |
|---|---|
| NaF | 1.00% |
| Amigel Thickener | 0.60% |
| Glycerol | 0.50% |
| Phenoxyethanol | 0.20% |
| 10% Phosphoric Acid | QS to pH |
| DI Water | QS to 100% |

Process A: The hair swatches are shampooed with Clarifying shampoo, towel blot and dried at medium heat with blow dryer. The Composition I Product was applied liberally to the hair with a tint brush and processed for 35 minutes. The excess product was towel blotted and the hair is dried to about 95% with a blow dryer at low heat followed with flat ironing @ 430° F. using 7-8 passes. The hair was rinsed after 48 hours. The performance % Curl Reduction, Shine and Smoothness was evaluated.

| Hair Type | pH | Lo (cm) | Ls (cm) | Lt (cm) | % Curl Reduction | Shine | Smoothness |
|---|---|---|---|---|---|---|---|
| Normal | 4.24 | 16.0 | 23.00 | 19.00 | 42.86% | + | + |
| | 4.53 | 15.5 | 23.00 | 18.00 | 33.33% | + | + |
| | 4.77 | 17.5 | 24.00 | 19.00 | 23.08% | + | + |
| 20Vol Color Treated | 4.24 | 21.0 | 26.50 | 22.50 | 27.27% | +++ | +++ |
| | 4.53 | 18.0 | 26.00 | 20.50 | 31.25% | ++ | ++ |
| | 4.77 | 19.0 | 25.00 | 19.50 | 8.33% | ++ | ++ |

TABLE IA-continued

| | | | | | | | |
|---|---|---|---|---|---|---|---|
| 2X 40 VOL BLEACHED HAIR | 4.24 | 17.5 | 24.00 | 19.50 | 30.77% | +++ | +++ |
| | 4.53 | 21.5 | 25.00 | 22.00 | 14.29% | ++++ | ++++ |
| | 4.77 | 18.5 | 23.50 | 20.00 | 30.00% | ++++ | ++++ |

Process B: The hair swatches are shampooed with Clarifying shampoo, towel blot and dried at medium heat with blow dryer. The composition I product was applied liberally to the hair with a tint brush and processed for 35 minutes. The excess product was towel blotted and hair was blow dried and straightened at high heat setting using a brush. The hair was rinsed after 48 hrs. The performance % Curl Reduction, Shine and Smoothness was evaluated.

| Hair Type | pH | Lo (cm) | Ls (cm) | Lt (cm) | % Curl Reduction | Shine | Smoothness |
|---|---|---|---|---|---|---|---|
| Normal | 4.24 | 13.5 | 20.0 | 16.5 | 30.00% | + | + |
| | 4.53 | 14.5 | 22.0 | 17.0 | 33.33% | + | + |
| | 4.77 | 13.0 | 23.0 | 18.0 | 50.00% | + | + |
| 20Vol Color Treated | 4.24 | 18.0 | 25.0 | 20.0 | 28.57% | +++ | +++ |
| | 4.53 | 15.5 | 22.5 | 17.5 | 28.57% | ++ | ++ |
| | 4.77 | 14.5 | 22.5 | 16.0 | 18.75% | ++ | ++ |
| 2X 40 VOL BLEACHED HAIR | 4.24 | 20.5 | 26.0 | 21.5 | 18.18% | +++ | +++ |
| | 4.53 | 19.5 | 26.0 | 22.0 | 38.46% | ++ | ++ |
| | 4.77 | 20.0 | 25.5 | 21.0 | 18.18% | ++ | ++ |

Process C: The hair swatches are shampooed with Clarifying shampoo, towel blot and dried at medium heat with blow dryer. The Composition I product was applied liberally to the hair with a brush and processed for 35 minutes. The excess product was towel blotted and air dried from the hair. The hair was rinsed after 48 hrs. The performance % Curl Reduction, Shine and Smoothness was evaluated.

| Hair Type | pH | Lo (cm) | Ls (cm) | Lt (cm) | % Curl Reduction | Shine | Smoothness |
|---|---|---|---|---|---|---|---|
| Normal | 4.24 | 17.0 | 27.0 | 20.0 | 30.00% | ++ | ++ |
| | 4.53 | 16.0 | 25.0 | 18.5 | 27.78% | ++ | ++ |
| | 4.77 | 16.0 | 25.0 | 18.0 | 22.22% | ++ | ++ |
| 20Vol Color Treated | 4.24 | 17.5 | 25.0 | 19.5 | 26.67% | +++ | +++ |
| | 4.53 | 16.0 | 24.0 | 18.0 | 25.00% | +++ | +++ |
| | 4.77 | 17.5 | 25.0 | 19.0 | 20.00% | +++ | +++ |
| 2X 40 VOL BLEACHED HAIR | 4.24 | 19.0 | 23.5 | 20.5 | 33.33% | ++++ | ++++ |
| | 4.53 | 19.5 | 22.5 | 20.0 | 16.67% | +++ | +++ |
| | 4.77 | 19.0 | 22.5 | 19.5 | 14.29% | +++ | +++ |

% Curl Reduction Evaluation:
L0 = Initial Length of curly hair
LS = Length of hair @ 100% Curl reduction
LT = Length of treated Curly hair
% Curl reduction = Lt − Lo × 100/Ls − L0
Shine and Smoothness:
Grading

| | |
|---|---|
| 0% | ± |
| 0-20% | + |
| 20-40% | ++ |
| 40-60% | +++ |
| 60-80% | ++++ |
| 80-100% | +++++ |

The tabulated data on Table IA shows that the optimum pH of Composition I for maximum performance is about 4.50. This is in agreement with the previous data of Table I. Exceptional curl reduction, smoothing and shine is observed on all hair types including Normal, Color treated and multi bleached hair.

TABLE II

Multi Treatment Effects of NaF versus Performance.
Performance Effects of 1 Treatment, 1 Wash, 5 Wash, 10 Wash and 2nd Treatment with 0.75% NaF Composition II-B on very curly/frizzy hair (Normal, Color treated and 2X Bleached Hair Type)

| COMPOSITION II-B | |
|---|---|
| NaF | 0.75% |
| Amigel Thickener | 0.60% |
| Glycerol | 0.50% |
| Phenoxyethanol | 0.20% |

TABLE II-continued

| | |
|---|---|
| 50% Phosphoric Acid | pH adjustment only |
| QS DI Water | QS. |

Process A: The hair swatches were shampooed with an alkaline shampoo (pH = 8.10), towel blot and dried at medium heat with blow dryer. The composition II-8 product was applied liberally to the hair with a tint brush and processed for 35 minutes. The excess product was towel blotted and the hair is dried to about 95% with a blow dryer at low heat followed with flat ironing @ 430° F. using 7-8 passes. The hair was rinsed after 48 hours. One of the swatch was rinsed and evaluated, the second swatch was washed 1 times and evaluated, the third swatch washed 5 times and evaluated, the fourth swatch was washed 10 times and evaluated and the fifth swatch was washed 10 times and 2nd treatment was repeated and after 48 Hours rinsed and evaluated for performance; % Curl Reduction; Shine and Smoothness.

| PERFORMANCE | | pH | $L_o$ (cm) | $L_s$ (cm) | $L_t$ (cm) | % Curl Reduction | Shine | Smoothness |
|---|---|---|---|---|---|---|---|---|
| NORMAL CURLY HAIR | 1 Treatment | 4.53 | 13.5 | 17.5 | 14.0 | 12.50% | +++ | ++ |
| | 1 Wash | 4.53 | 13.5 | 17.0 | 13.5 | 0.00% | ++ | ++ |
| | 5 wash | 4.53 | 13.5 | 17.0 | 13.5 | 0.00% | ++ | ++ |
| | 10 Wash | 4.53 | 13.0 | 17.5 | 13.0 | 0.00% | ++ | ++ |
| | 2nd treatment | 4.53 | 14.0 | 18.5 | 15.0 | 22.22% | +++ | +++ |
| 20 VOL /6R COLOR TREATED HAIR | 1 Treatment | 4.53 | 13.5 | 18.5 | 14.0 | 10.00% | +++ | +++ |
| | 1 Wash | 4.53 | 13.5 | 18.5 | 14.0 | 10.00% | ++ | ++ |
| | 5 wash | 4.53 | 13.5 | 19.0 | 14.0 | 9.09% | ++ | ++ |
| | 10 Wash | 4.53 | 13.5 | 18.5 | 13.5 | 0.00% | ++ | ++ |
| | 2nd treatment | 4.53 | 13.5 | 18.0 | 14.5 | 22.22% | +++ | +++ |
| 2X BLEACHED HAIR 40 VOL | 1 Treatment | 4.53 | 15.0 | 20.5 | 16.0 | 18.18% | ++++ | ++++ |
| | 1 Wash | 4.53 | 15.0 | 20.0 | 16.0 | 20.00% | +++ | +++ |
| | 5 wash | 4.53 | 16.0 | 21.0 | 16.0 | 0.00% | ++ | ++ |
| | 10 Wash | 4.53 | 15.0 | 20.5 | 15.0 | 0.00% | ++ | ++ |
| | 2nd treatment | 4.53 | 16.0 | 20.5 | 18.5 | 55.56% | ++++ | ++++ |

% Curl Reduction Evaluation:
$L_o$ = Initial Length of curly hair
$L_s$ = Length of hair @ 100% Curl reduction
$L_t$ = Length of treated Curly hair $$\% \text{ Curl reduction} = \frac{L_t - L_o}{L_s - L_o} \times 100$$

Shine and Smoothness Evaluation:
Grading

| | |
|---|---|
| 0% | ± |
| 0-20% | + |
| 20-40% | ++ |
| 40-60% | +++ |
| 60-80% | ++++ |
| 80-100% | +++++ |

The tabulated data on Table II shows that the performance longevity of a single treatment with Composition II-B can last multiple shampoos. In addition, the performance of repeat or double treatments increases significantly the performance in curl reduction, shine and smoothness.

TABLE III

Phase II-B- Effects of NaF pH on performance
Curl Reduction Study at Higher pH Range with 0.50% NaF Composition II-B on very curly/frizzy hair
(Normal, Color treated and 2X Bleached Hair Type)

| COMPOSITION II-B | |
|---|---|
| NaF | 0.50% |
| Amigel Thickener | 0.60% |
| Glycerol | 0.50% |
| Phenoxyethanol | 0.20% |
| 50% Phosphoric Acid | pH adjustment only |
| QS DI Water | QS. |

Process A: The measurement of the initial length ($L_0$) and ($L_{100}$) of each swatch was taken. The hair swatches were shampooed with Clarifying Shampoo, towel blot and dried at medium heat with blow dryer. The Composition 11 "B" with different pH range was applied liberally to the hair with a tint brush and processed for 35 minutes. The excess product was towel blotted and the hair is dried to about 95% with a blow dryer at high heat followed by flat ironing @ 430° F. using 7-8 passes. The hair was rinsed after 48 hours and air dried. % Curl Reduction was calculated with the final length ($L_t$) of each swatch after treatment. The results are as follows.

TABLE III-continued

| pH Range | | pH | $L_o$ (cm) | $L_s$ (cm) | $L_t$ (cm) | % Curl Reduction |
|---|---|---|---|---|---|---|
| 4.51 | Normal hair | 4.51 | 12.5 | 17.5 | 13.5 | 20.00% |
| | 20 Vol/CT | 4.51 | 15.0 | 20.0 | 16.5 | 30.00% |
| | 2X Bleached | 4.51 | 15.0 | 16.5 | 16.0 | 66.67% |
| 8.67 | Normal hair | 8.67 | 13.0 | 20.0 | 14.0 | 14.29% |
| | 20 Vol/CT | 8.67 | 14.0 | 19.5 | 16.0 | 36.36% |
| | 2X Bleached | 8.67 | 15.5 | 16.5 | 16.0 | 50.00% |
| 9.05 | Normal hair | 9.05 | 12.5 | 18.5 | 14.5 | 33.33% |
| | 20 Vol/CT | 9.05 | 14.0 | 19.0 | 15.5 | 30.00% |
| | 2X Bleached | 9.05 | 15.5 | 16.5 | 16.2 | 70.00% |

% Curl Reduction Evaluation:
$L_o$ = Initial Length of curly hair
$L_s$ = Length of hair @ 100% Curl reduction
$L_t$ = Length of treated Curly hair $$\% \text{ Curl reduction} = \frac{L_t - L_o}{L_s - L_o} \times 100$$

The data of Table III shows the performance of Composition IIB, 0.50% NaF above pH 8.05 shows no advantages. This is probably due to unfavorable crosslinking between unprotonated amino R'—N—R" (R'=H, C=0 or R"=H, C=0) peptide side terminals and the Fluoride ion that occurs at high pH. Whereas the pH decreases the protonation of the amino group and specifically the peptide side terminals of Lysine, Arginine R—NH3+ and will favor crosslinking with the Fluoride ion. These side terminal crosslinks R—NH₃F, —N—H2F, —N—HF or possible amide crosslinks F—N—C=O are more favorable at low pH. Alternatively, favorable crosslinking may occur with the side OH side terminals of Threonine and Serine or indirect crosslinking followed by dehydration for Threonine side terminal.

TABLE IV

Effects of NaF Concentration on Performance versus Formaldehyde @ 0.5%
PERFORMANCE EFFECTS OF % MCLA ON VERY CURLY/FRIZZY HAIR
(NORMAL CURLY, COLOR TREATED AND 2X BLEACHED HAIR TYPE)

COMPOSITION II

| | |
|---|---|
| NaF | 0.5-2.5% |
| Amigel Thickener | 0.60% |
| Glycerol | 0.50% |
| Phenoxyethanol | 0.20% |
| 10% Phosphoric Acid | pH adjustment only |
| QS DI Water | QS. |

Process A: The hair swatches are shampooed with Clarifying shampoo, towel blot and dried at medium heat with blow dryer. The Composition II product was applied liberally to the hair with a tint brush and processed for 35 minutes. The excess product was towel blotted and the hair is dried to about 95% with a blow dryer at low heat followed with flat ironing @ 430° F. using 7-8 passes. The hair was rinsed after 48 hours. The performance % Curl Reduction, Shine and Smoothness was evaluated.

| PERFORMANCE | % NaF | Swatch | pH | Lo (cm) | Ls (cm) | Lt (cm) | % Curl Reduction | Shine | Smoothness |
|---|---|---|---|---|---|---|---|---|---|
| NORMAL CURLY HAIR | 0.50% | A | 4.49 | 14.0 | 25.0 | 17.0 | 27.27% | xxx | xxx |
| | 0.75% | M | 4.52 | 15.0 | 24.0 | 18.0 | 33.33% | xx | xx |
| | 1.00% | B | 4.51 | 14.5 | 23.0 | 17.0 | 29.41% | xxx | xxx |
| | 1.50% | C | 4.49 | 14.0 | 23.0 | 16.5 | 27.78% | xx | xx |
| | 2.00% | D | 4.51 | 14.0 | 25.0 | 16.5 | 22.73% | xx | xx |
| | 2.50% | E | 4.48 | 14.0 | 25.0 | 16.5 | 22.73% | xx | xx |
| 0.5% Formaldehyde | 0.00% | FORM | 4.5 | 15.0 | 24.0 | 18.5 | 38.89% | xx | xx |
| 20 VOL COLOR TREATED HAIR | 0.50% | A | 4.49 | 16.0 | 24.0 | 18.5 | 31.25% | xxx | xxx |
| | 0.75% | M | 4.52 | 13.0 | 20.5 | 15.0 | 26.67% | xx | xx |
| | 1.00% | B | 4.51 | 16.0 | 23.0 | 18.0 | 28.57% | xx | xx |
| | 1.50% | C | 4.49 | 16.0 | 24.0 | 18.0 | 25.00% | xx | xx |
| | 2.00% | D | 4.51 | 16.0 | 22.0 | 18.0 | 33.33% | xx | xx |
| | 2.50% | E | 4.48 | 16.0 | 23.5 | 18.5 | 33.33% | xxx | xxx |
| 0.5% Formaldehyde | 0.00% | FORM | 4.5 | 13.0 | 21.0 | 15.5 | 31.25% | xx | xx |
| 2X 40 VOL BLEACHED HAIR | 0.50% | A | 4.49 | 19.0 | 23.0 | 20.5 | 37.50% | xxx | xx |
| | 0.75% | M | 4.52 | 18.0 | 23.0 | 20.0 | 40.00% | xxx | xxx |
| | 1.00% | B | 4.51 | 20.5 | 25.0 | 22.0 | 33.33% | xxx | xxx |
| | 1.50% | C | 4.49 | 21.0 | 25.0 | 22.5 | 37.50% | xxx | xxx |
| | 2.00% | D | 4.51 | 20.0 | 23.0 | 21.0 | 33.33% | xx | xx |
| | 2.50% | E | 4.48 | 18.0 | 23.0 | 20.0 | 40.00% | xx | xx |
| 0.5% Formaldehyde | 0.00% | FORM | 4.5 | 18.0 | 23.0 | 20.5 | 50.00% | xxx | xxx |

TABLE IV-continued

Process D: The hair swatches are shampooed with shampoo, towel blot and dried at medium heat with blow dryer. The composition II product was applied liberally to the hair with a brush and processed for 35 minutes. The hair was rinsed with luke warm water. The hair is dried to about 95% with a blow dryer at low heat followed with flat ironing at 430° F. using 7-8 passes. The hair was rinsed after 48 hours. The performance % Curl Reduction, Shine and Smoothness was evaluated.

| PERFORMANCE | % MCLA | | pH | Lo (cm) | Ls (cm) | Lt (cm) | % Curl Reduction | Shine | Smoothness |
|---|---|---|---|---|---|---|---|---|---|
| NORMAL CURLY HAIR | 0.50% | A | 4.49 | 13.50 | 20.00 | 14.50 | 15.38% | xxx | xxx |
| ($H_2PO_4$) | 0.75% | M | 4.52 | 15.00 | 25.00 | 18.00 | 30.00% | xx | xx |
| | 1.00% | B | 4.51 | 13.50 | 20.50 | 15.00 | 21.43% | xx | xx |
| | 1.50% | C | 4.49 | 12.00 | 20.00 | 14.00 | 25.00% | xx | xx |
| | 2.00% | D | 4.51 | 13.00 | 21.00 | 15.00 | 25.00% | xx | xx |
| | 2.50% | E | 4.48 | 12.00 | 21.50 | 14.50 | 26.32% | xxx | xxx |
| 0.5% Formaldehyde | 0.00% | FORM | 4.5 | 12.00 | 19.00 | 14.50 | 35.71% | xx | xx |
| 20 VOL COLOR TREATED | 0.50% | A | 4.49 | 17.00 | 24.50 | 18.00 | 13.33% | xxx | xxx |
| HAIR | 0.75% | M | 4.52 | 14.00 | 22.00 | 16.00 | 25.00% | xx | xx |
| | 1.00% | B | 4.51 | 15.00 | 23.00 | 17.00 | 25.00% | xxx | xxx |
| | 1.50% | C | 4.49 | 16.00 | 23.00 | 17.00 | 14.29% | xx | xxx |
| | 2.00% | D | 4.51 | 16.00 | 23.00 | 17.00 | 14.29% | xx | xxx |
| | 2.50% | E | 4.48 | 15.50 | 23.00 | 17.00 | 20.00% | xx | xxx |
| 0.5% Formaldehyde | 0.00% | FORM | 4.5 | 14.00 | 22.00 | 17.00 | 37.50% | xx | xx |
| 2X 40 VOL BLEACHED | 0.50% | A | 4.49 | 15.00 | 19.00 | 16.50 | 37.50% | xx | xxx |
| HAIR | 0.75% | M | 4.52 | 20.00 | 23.50 | 21.00 | 28.57% | xx | xxx |
| | 1.00% | B | 4.51 | 16.00 | 20.00 | 17.00 | 25.00% | xx | xxx |
| | 1.50% | C | 4.49 | 16.00 | 20.00 | 17.00 | 25.00% | xx | xxx |
| | 2.00% | D | 4.51 | 15.00 | 19.00 | 16.00 | 25% | xx | xxx |
| | 2.50% | E | 4.48 | 15.00 | 20.00 | 16.50 | 30.00% | xx | xxx |
| 0.5% Formaldehyde | 0.00% | FORM | 4.5 | 20.00 | 24.00 | 21.50 | 37.50% | xx | xxx |

% Curl Reduction Evaluation:
L0 = Initial Length of curly hair
LS = Length of hair @ 100% Curl reduction
LT = Length of treated Curly hair
% Curl reduction = Lt − Lo × 100/Ls − L0
Shine and Smoothness Evaluation:
Grading

| | |
|---|---|
| 0% | ± |
| 0-20% | + |
| 20-40% | ++ |
| 40-60% | +++ |
| 60-80% | ++++ |
| 80-100% | +++++ |

The tabulate data of Table IV shows that the performance on normal hair is not affected greatly with the concentration increase of NaF from 0.5-2.50%. However, on porous hair 20 volume and twice 40 volume bleached hair, NaF concentration effects are observed. The data shows equivalent performance to 0.5% Formaldehyde is obtained with 0.23% F (0.50% NaF). This observation can be explained due to the presence of larger number of Ionic sites in hair which result in greater crosslinking and overall performance of curl reduction and smoothing effects. It also suggests that the crosslinking reactions of the fluoride and formaldehyde with hair may not entirely be the same. The specificity of crosslinking with the fluoride is greater than formaldehyde, thus more predictable results can be obtained.

TABLE V

Performance Evaluation using Treatment Processes E, F and G (Normal, Color treated and 2X Bleached Hair Type)

COMPOSITION II-B

| | |
|---|---|
| NaF | 0.75% |
| Amigel Thickener | 0.60% |
| Glycerol | 0.50% |
| Phenoxyethanol | 0.20% |
| 50% Phosphoric Acid | pH adjustment only |
| QS DI Water | QS. |

| PERFORMANCE | | pH | $L_o$ (cm) | $L_s$ (cm) | $L_t$ (cm) | % Curl Reduction | Shine | Smoothness |
|---|---|---|---|---|---|---|---|---|
| NORMAL CURLY HAIR | Process E | 4.49 | 13.0 | 20.0 | 14.5 | 21.43% | ++ | ++ |
| | Process F | 4.49 | 13.0 | 20.0 | 15.0 | 28.57% | +++ | +++ |
| | Process G | 4.49 | 13.0 | 20.0 | 15.0 | 28.57% | +++ | +++ |
| 20 VOL /6R | Process E | 4.49 | 10.0 | 13.5 | 11.0 | 28.57% | ++ | ++ |
| COLOR TREATED HAIR | Process F | 4.49 | 10.0 | 13.5 | 11.0 | 28.57% | ++++ | ++++ |
| | Process G | 4.49 | 13.0 | 20.0 | 15.0 | 28.57% | ++++ | ++++ |

TABLE V-continued

| | | | | | | | | |
|---|---|---|---|---|---|---|---|---|
| 2X BLEACHED HAIR | | Process E | 4.49 | 14.0 | 18.0 | 16.0 | 50.00% | ++ | ++ |
| | | Process F | 4.49 | 14.0 | 18.0 | 16.0 | 50.00% | ++++ | ++++ |
| 40 VOL DIFFERENT PROCESSES TESTED | | Process G | 4.49 | 14.0 | 18.0 | 16.0 | 50.00% | ++++ | ++++ |

Process E: Wash hair with clarifying shampoo. Towel blot excess water and blow dry in medium heat up to 95% dry. Apply the Fluoride product thoroughly and comb hair through to ensure that all hair fibers are saturated with the product. Process for 35 min. Keep the hair straight during process time. Rinse with luke warm water and towel blot excess water. Apply a Moisturizing Leave-on Conditioner and detangle the hair with the comb. Blow dry hair in high heat. Take thin sections and flat iron at approximately 430° F. with 7-8 passes, make sure that all the fibers are passed through the heat evenly. After 48 hours wash hair with Sulfate Free Shampoo and Conditioner.
Process F
Wash hair with clarifying shampoo. Towel blot excess and blow dry in medium heat up to 95% dry. Apply the Fluoride product thoroughly and comb hair through to ensure that all hair fibers are saturated with the product. Process for 35 min. Keep the hair straight during process time. Towel blot excess product and apply a deep conditioning masque. Comb through so that all the fibers are covered with masque. Process for 10 min and rinse with Luke warm water. Towel blot excess water and Blow dry in high heat. Take thin sections and flat iron at approximately 430° F. with 7-8 passes, make sure that all the fibers are passed through the heat evenly.
After 48 hours wash hair with Sulfate Free Shampoo and Conditioner.
Process G
Wash hair with Clarifying shampoo. Towel blot excess and blow dry in medium heat up to 95% dry. Apply the Fluoride product thoroughly with a tint brush. Comb hair through to ensure that all hair fibers are saturated with the product. Process for 35 min. Keep the hair straight during process time. Towel blot excess product and apply a Leave-On Conditioner. Comb through so that all the fibers are saturated. Towel blot excess and blow dry up to 95% dry. Take very thin sections and flat iron at approximately 430° F. with 7-8 passes, make sure that all the fibers are passed through the heat evenly. Section Hair and apply the deep conditioning masque and process for 10 minutes. Rinse with Luke warm water and style as desired.

% Curl Reduction Evaluation:
$L_o$ = Initial Length of curly hair
$L_s$ = Length of hair @ 100% Curl reduction
$L_t$ = Length of treated Curly hair $$\% \text{ Curl reduction} = \frac{L_t - L_o}{L_s - L_o} \times 100$$

Shine and Smoothness Evaluation:
Grading

| | |
|---|---|
| 0% | ± |
| 0-20% | + |
| 20-40% | ++ |
| 40-60% | +++ |
| 60-80% | ++++ |
| 80-100% | +++++ |

The data in Table V shows the different methods of treatment application to enhance the conditioning effects with the fluoride treatment. All treatment methods E, F and G increase the conditioning and smoothing effects of hair. Based on the results it appears that method G is the best where the fluoride is crosslinked first to the hair and the conditioning agents are further crosslinked by the fluoride. This multi-crosslinking effect of fluoride between the hair and the conditioning agent creates longer lasting effects between washes. Comparative results with just hair conditioning treatments of masking or rinse off conditioners shows a temporary effect that does not last more than one or two shampoos. The fluoride crosslinked hair will have a strong affinity to bind different molecules, such as conditioning, antistatic, volumizing ingredients, keratin proteins and non-keratinous proteins. The crosslinking of fluoridated keratin reacts with functional groups of strong cationic character, such amino, mono or divalent cations forming strong ligand structures within the hair. The formation of these additional structures will restructure hair and produce effects of increased softness, manageability and tensile strength.

Methods of Sodium Fluoride Application on Hair for Maximum Conditioning/Smoothing Effects
Process E:
Wash the hair with Clarifying shampoo. Towel blot excess and blow dry in medium heat up to 95% dry. Apply the Fluoride composition product on hair thoroughly. and comb through to ensure that all the fibers are saturated with the product. Process for 35 min. Keep the hair straight during process time. Rinse with luke warm water and towel blot excess water. Apply a Leave-on Conditioner and detangle the hair with the comb. Blow dry with medium heat. Take thin sections and iron hair with a preheated flat iron with a minimum of 7-8 passes, making sure that all the fibers are passed through evenly. After 48 hours wash hair with Sulfate Free Shampoo and Conditioner.
Process F:
Wash the hair with Clarifying shampoo. Towel blot excess and blow dry in medium heat up to 95% dry. Apply the Fluoride composition product on hair thoroughly and comb through to ensure that all the fibers are saturated with the product. Process for 35 min. Keep the hair straight during process time. Towel blot excess product and apply a deep conditioner, reconstructor or conditioning masque with a tint brush. Comb through so that all the fibers are covered with deep conditioner, reconstructor or conditioning masque. Process for 10 min and rinse with luke warm water. Towel blot excess water and blow dry with high heat. Take thin sections and iron hair with a pre-heated flat iron with a minimum of 7-8 passes, making sure that all the fibers are passed through evenly. After 48 hours wash hair with Sulfate Free Shampoo and Conditioner.
Process G:
Wash hair with Clarifying shampoo. Towel blot excess and blow dry hair in medium heat up to 95% dry. Apply the fluoride composition product on hair thoroughly and comb through to ensure that all the fibers are saturated with the product. Process for 35 min. Keep the hair straight during process time. Towel blot excess product and apply a Leave- On Conditioner. Comb through so that all the fibers are saturated. Towel blot excess and blow dry up to 95% dry. Take very thin sections and iron hair with a pre heated flat iron with a minimum of 7-8 passes, making sure that all the fibers are passed through evenly. Section Hair and apply a deep conditioner, reconstructor or conditioning masque and process for 10 minutes. Rinse with luke warm water and style as desired.

Moisturizing Leave on Conditioner Formula
Water
Amodimethicone
Glycine
Hydrolyzed Keratin
Hydrolyzed Silk
Hydrolyzed Vegetable Protein
Retinyl Palmitate
Ascorbic Acid
Benzophenone-4
Butylene Glycol
Ceteareth 25
Cetrimonium Chloride
Lecithin
Polyquaternium-11
Propylene Glycol
Steartrimonium Chloride
Sucrose
Tetrasodium EDTA
VP/VA Copolymer
Isopropyl alcohol
Fragrance Deep Conditioning Masque Formula
Water
PPG-3 Benzyl Ether Myristate
Cyclopentasiloxane
Dimethicone
Cetearyl Alcohol
Behentrimonium Chloride
Panthenol
Hydrolyzed Keratin
Sodium PCA
Sodium Lactate
VP/DMAPA/Acrylates Copolymer
Cetrimonium Chloride
Phenoxyethanol
Caprylyl Glycol
Ethylhexyl glycerine
Hexylene Glycol
Fragrance During our testing it was discovered that the cross linker composition containing sodium fluoride had insufficient conditioning for combing and flat ironing of hair during the treatment. The conditioning was improved by applying conditioning compositions on the hair after the application of the crosslinker composition but suffered from inconsistent results due to the heterogeneous product on the hair. It was found for optimum consistent performance a homogeneous cross linker composition with conditioning agents was necessary. The key conditioning agents, such as phenyl trimethicone, amodimethicone, polyquaternium-67 and cetrimonium chloride, were required but not limited. However, the ready to use crosslinker/conditioning composition presented stability/performance issues. We currently believe that this was due to a change of the crosslinking affinity of the fluoride to the hair by the conditioning agents. In order to alleviate this premixing of the crosslinking composition with a conditioning composition was developed where the cross linker composition part 1 is mixed with the conditioning composition part 2 at ratios by weight of 10:90, 40:60, 55:45, 75:25 and 95:5. Where the preferable composition would be 75:25. Two treatment processes H and I resulted in excellent smoothing results in our studies for up to three months. Both processes include the rinse off and a leave on conditioner for final sealing and smoothing of hair. For extended smoothing results the leave-on conditioner is used once or twice a week after shampooing and conditioning the hair.

Process H:

Wash hair with clarifying shampoo. Towel blot and blow dry hair to about 90%. Premix Composition Part 1 and Part 2 at ratio of about 75:25 by weight.

Apply the premixed product on the hair. Comb through to ensure that all the fibers are saturated with the product. Process for 35 min. Keep the hair straight during the processing time. Towel blot excess product and blow dry hair to about 90%. Take thin sections and flat iron at approximately 430° F. with about 7-8 passes, make sure that all the fibers are passed through the heat evenly. Apply a deep conditioning masque through the hair and wait for approximately 7-10 minutes.

Comb through so that all the fibers are covered with the deep conditioner. Process for 10 min and rinse with lukewarm water and style as desired. After 48 hours wash hair with sulfate free shampoo and conditioner and style as desired.

Process G:

Wash the hair with clarifying shampoo. Towel blot and blow dry hair to about 90%. Premix Composition Part 1 and Part 2 at ratio of about 75:25 by weight.

Apply the premixed product on the hair. Comb through to ensure that all the fibers are saturated with the product. Process for 35 min. Keep the hair straight during the processing time. Towel blot excess product and blow dry hair to about 90%. Take thin sections and flat iron approximately 430° F. with about 7-8 passes, make sure that all the fibers are passed through the heat evenly. Apply a leave-on conditioner through the hair and wait for approximately 7-10 minutes. Comb hair through so that all the fibers are covered with the conditioner. Process for about 10 minutes, remove excess and style as desired. After about 48 hours wash hair with sulfate free shampoo and conditioner and style as desired.

| Composition Part 1 | |
| --- | --- |
| | (w/w) % |
| Water | 95.17 |
| Phosphoric Acid | 1.70 |
| NaF | 1.33 |
| Phenoxyethanol | 0.80 |
| Glycerine | 0.50 |
| Hydroxypropyl Guar | 0.50 | pH = 4.50

| Composition Part 2 | |
| --- | --- |
| | (w/w) % |
| Water | 85.22 |
| Alcohol Denatured | 4.62 |
| Cetrimonium Chloride | 1.24 |
| Phenyltrimethicone | 1.00 |
| Phenoxyethanol | 0.80 |

-continued

| Composition Part 2 | |
|---|---|
| | (w/w) % |
| Amodimethicone | 0.63 |
| Trideceth-12 | 0.27 |
| Polyquaternium-67 | 0.55 |
| VP/VA Copolymer | 0.30 |
| Polyquaternium-11 | 0.30 |
| Fragrance | 0.10 |
| Steartrimonium Chloride | 0.023 |
| Isopropyl Alcohol | 0.012 | pH = 5.65

| Leave-On Conditioner | |
|---|---|
| | (w/w) % |
| Water | 93.69 |
| Hydrolyzed Quinoa Protein | 1.00 |
| Phenoxyethanol | 0.50 |
| Glycerin | 0.50 |
| Hydroxyethyl Cetyldimonium phosphate | 1.00 |
| Cetrimonium Chloride | 0.75 |
| Polyquaternium-28 | 1.00 |
| Amodimethicone Trideceth-12 | 1.00 |
| Stearyldimonium hydroxyl propyl Lauryl | 0.50 |
| Panthely Hydroxypropyl Sreardimonium Chloride | 0.20 |
| Polyquaternium-22 | 0.20 |
| Fragrance | 0.05 |
| VP/DMAPA Acrylates Copolymer | 0.10 |
| Dimethicone/Silica | 0.02 |
| Phosphoric acid | QS to pH | pH = 5.73

TABLE VI

Detection of Fluoride Ion in Normal, Colored and Bleached Single Treated Hair Fibers with Composition II, 0.75% Na F @ pH 4.51
Analysis of fluoride ion in single treated hair initially and after multiple washes with smoothing shampoo and conditioner.
µg Fluoride/g Hair

| 0.75% NaF | 1 Treatment | 3 Wash | 5 Washes | 10 Washes | 15 Washes |
|---|---|---|---|---|---|
| Normal Control | 0 | 0 | 0 | 0 | 0 |
| Normal Treated | 3529 | 2875 | 2662 | 2564 | 2046 |
| Color Treated Control | 0 | 0 | 0 | 0 | 0 |
| Color Treated Treated | 3380 | 3673 | 3892 | 3393 | 2796 |
| 2x Bleached Control | 0 | 0 | 0 | 0 | 0 |
| 2x Bleached Treated | 1876 | 1374 | 802 | 845 | 1007 |

Hair type: Normal, 20vol/6R Color Treated and 2X Bleached hair.
Variations: 1 treatment; 3 wash; 5 wash; 10 wash and 15 washes
Buffer Solution: 25 ml. TISAB II + 25 ml. DI $H_2O$ for immersing the hair sample for 48 hours.
Standards for Calibration: 2, 4, 6, 10, 20 (µg/ml) Fluoride Ion
Detection Limit = <0.1 (µg/ml) Fluoride Ion
Procedure:
All the hair swatches were washed with an Alkaline Shampoo at pH 8.09. The controls and the samples to be treated were dried to 95% with blow dryer, at medium heat setting. The hair swatches (approximately 5 inch in width) were treated with composition II (0.75% NaF) pH = 4.51. Processed for 35 min. Towel blot excess. Dried up to 95% dry with blow dryer at medium heat followed with flat ironing small sections of hair at approximately 430° F. with 7-8 passes. After 48 hours the hair was rinsed with copious amounts of water and hair was dried at ambient conditions and cut into small 1/16" sections. The hair was further equilibrated under ambient conditions for 8 hours and hair samples weighed about 0.5 grams and were immersed into 50 ml of buffer solutions 1:1 Total Ionic Strength Adjustment Buffer (TISAB II): Deionized Water for 48 hours. Direct analysis of the Fluoride Ion was carried out in the leached solutions using the Fluoride Ion Selective Electrode potentiometric method (ASTM D 1179-72) approved by the American Society of Testing and Materials. The hair swatches were washed 3x, 5x, 10x and 15 x, and the hair was dried with blow dryer between the washes. The multi washed hair samples were analyzed as above.

The data in Table VI shows that fluoride is detected in normal, colored and bleached hair treated hair. Based on the assay results about 3,400 µmoles F/g hair is detected in water/buffer leaches of normal and color treated hair. This is compared to 1,800 µmoles F/g hair for bleached hair. This detection of fluoride in treated hair even after fifteen washes suggest that stable crosslinking has occurred and it is resistant to conventional shampooing and conditioning. The detection of fluoride in the buffer/water leaches is about 42-46% after fifteen shampoos showing slow rate of depletion or leaching of fluoride from hair. Based on these observations long lasting results of up to fifteen or more shampoos should be expected from a single treatment.

TABLE VII pH EFFECTS OF 1% NaF ON THE TENSILE STRENGTH OF NORMAL, COLOR TREATED AND 2X BLEACHED HAIR
20% INDEX

| pH | Normal Hair | 20 Volume Hair | 2x Bleached Hair |
|---|---|---|---|
| 3.51 | 0.977 | 0.932 | 0.788 |
| T-Test @pH 3.51 | P = 0.0028* | P = 0.041* | P = 0.00024* |
| 4.49 | 0.982 | 0.936 | 0.759 |
| T-Test @pH 4.51 | P = 0.00005* | P = 0.036* | P = 0.00413* |
| 6.01 | 0.980 | 0.925 | 0.756 |
| T-Test @pH 6.20 | P = 0.0040* | P = 0.069 | P = 0.0058* |
| 7.62 | 0.966 | 0.910 | 0.744 |
| T-Test @pH 7.62 | P = 0.132 | P = 0.0082* | P = 0.0118* |
| Brazilian Blowout Solution; @pH 3.77 8% Formaldehyde | 0.820 | | |
| T-Test | P = 0.0143* | | |
| Untreated Hair | 0.959 | 0.834 | 0.707 |

*statistically significant difference from untreated hair
Procedure:
Hair for tensile testing was prepared with five bundles of twelve hair fibers (total of 60 fibers) of similar texture with Normal, 20 Volume, 2x Bleached hair. The bundles were immersed in water for 1-2 hours and the initial wet tensile strength of all the bundles was evaluated at 20% extension using an Instron Model 1122C5054 at 0.5 inch/minute. The bundles after 24 hours were washed, blow dried with a paddle brush to about 95% and the NaF Composition I at pH 4.50 was applied with the tint brush and processed for 35 minutes. After the excess product was towel blotted and blow dried to about 95% with medium heat using a paddle brush, each bundle were flat ironed at approximately 430° C. with 7-8 passes. After 24 hours, the fibers were soaked in DI water and after 45 minutes the tensile strength of bundles was determined under the identical conditions. The tensile strength of bundles was determined versus untreated fibers with composition I. The wet tensile strength of each bundle was calculated as 20% index given below:
20% Index = Force of hair fibers after treatment/Force of hair fibers after treatment The tensile strength studies showed that statistically a single treatment of normal, colored and bleached hair with the fluoride composition I statistically and significantly improved the tensile strength. The wet strength is attributed by adding support to the alpha helical crosslinks of cystine. This is not an expected effect for wet strength since all secondary bonds should be minimized in water. It is interesting that formaldehyde has significantly decreased the tensile strength of hair which suggests the weakening of these crosslinks. This supports our understanding that the crosslinking reactions and mechanism between the fluoride and formaldehyde is different.

Differential Scanning Calorimetry (DSC) of Hair

Differential scanning calorimetry (DSC) techniques published earlier by Cao (J. Cao, Melting study of the a crystallites in human hair by DSC, Thermody. Acta, 335 (1999) and F. J. Wortmann, (F. J Wortmann, C. Springob, and G. Sendlebach, Investigations of cosmetically treated human hair by DSC in water, IFFCC.Ref 12 (2000) are used to study the structural changes of hair by measuring the thermal decomposition pattern or behavior. The thermal stability of hair is evaluated by measuring the amount of thermal energy required for denaturation or phase transition. The technique measures the amount of heat transferred into and out of a sample in a comparison to a reference. The heat transfer in (endothermic) and out (exothermic) is detected and recorded as a thermogram of heat flow versus temperature.

The technique gives valuable information on the morphological components of hair of Feughelman's accepted two phase filament matrix model for hair (M Feugelman, *A two phase structure for keratin fibers*, Text. Res. 1, 29, 223-228, 1959). This two phase model includes the crystalline filaments (alpha helical proteins) or traditionally referred to as microfibrils which are embedded in an amorphous matrix.

The DSC data technique yields thermogram data on the denaturation temperature $T_m$ and the denaturation enthalpy (delta H) of hair. It is concluded that the thermogram data of the denaturation temperature $T_m$ of hair is dependent on the crosslink density of the matrix in which surrounds the microfibrils or crystalline filaments. Also, the denaturation enthalpy (delta H) depends on the strength of the crystalline filaments or microfibrils. It has been shown that cosmetic treatments, such as bleaching or perming, effect these morphological components selectively and differently at different rates causing changes in denaturation temperatures and in heat flow.

DSC was use to analyze the effects of NaF treatment on Normal, 20 volume color treated and four times bleached hair. The treatment included Process A using Composition I at 1% NaF at pH 4.50. The hair after 48 hours was rinsed and dried at ambient temperature conditions and relative humidity (20° C., 65% RH). The hair samples were cut into small pieces of about 2 mm in length and about 4-7 mg weighed into aluminum pans followed with capping. The hair samples were analyzed using Perkin Elmer Diamond DSC instrument and a method of 50° C. to 280° C. at 20° C./minute using an empty capped aluminum pan as reference.

The obtained DSC thermograms for treated and untreated hair samples showed single endothermic (absorbed thermal energy) denaturation temperatures $T_m$ ranging from 178 to 189° C. and delta H from 154 to 340 (J/g). The comparative tabulated data below for normal untreated and treated hair shows differences in the denaturation temperatures of 178.88 and 184.33° C., respectively, with no differences in the delta H. This is due to changes in the crosslink density of the matrix attributed by an increase in the crosslink density of the matrix proteins with NaF. Based on the delta H it is assumed that the intermediate filaments or alpha helical protein regions or microfilaments are not affected. The results for 20 volume color treated and untreated hair show significant statistically changes in the delta H (p=0.00019) of 226.53 and 270.01 (J/g) and no changes in the denaturation temperature. This observation suggests that the effects of NaF on 20 volume color treated hair are primarily on the alpha helical protein regions with no effect on the matrix proteins. The multi bleached hair fibers show statistically differences in the denaturation temperatures 187.76 and 181.49° C. and delta H 260.28 and 318.16 (J/g) between untreated and treated samples. This observation suggests that both the matrix proteins and the alpha-helical proteins are affected by the NaF treatment. This data is in good agreement with previously reported data by Humphries et al. JSCC, 1972 on oxidized and colored dried hair showing higher denaturation temperatures and delta H. The explanation may be explained by an increase in crosslinked bridges between the polypeptide chains giving more structural support. This appears to be the same observation with the NaF increasing the overall support for hair through crosslinking on the matrix proteins and alpha helical regions of the hair.

Endotherm

| HAIR | Peak Temperature (C°) | Delta H (J/g) |
|---|---|---|
| Normal | 178.88 ± 1.80 | 154.98 ± 6.23 |
| Normal (Treated) | 184.33 ± 1.88 | 159.06 ± 3.65 |
| T-Test Normal Hair | P = 0.06892 | P = 0.315 |
| 20 Volume | 181.84 ± 2.63 | 226.53 ± 1.14 |
| 20 Volume (Treated) | 182.94 ± 3.07 | 270.01 ± 2.53 |
| T-Test 20 Volume Hair | P = 0.588 | P = 0.00019 |
| 4x Bleached Hair | 187.76 ± 1.51 | 260.28 ± 10.19 |
| 4X Bleached Hair (Treated) | 181.49 ± 0.93 | 318.16 ± 22.07 |
| T-Test Bleached Hair | P = 0.00033 | P = 0.015 |

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances that fall within the scope of the disclosure.

What is claimed is:

1. A hair care composition comprising:
   a crosslinking component comprising an inorganic fluoride selected from the group consisting of sodium fluoride, potassium fluoride, ammonium fluoride, lithium fluoride, zirconium fluoride, nickel fluoride, ammonium hexafluorophosphate, sodium monofluorophosphate, and any combinations thereof, and which is present in an amount of 0.1% to 3.0%, based on the total weight of the composition; and
   a conditioning component, wherein said conditioning component is selected from the group consisting of amodimethicone, cyclomethicone, dimethicone, behentrimonium methosulfate, citrimonium chloride, citrimonium bromide, cocotrimonium methosulfate, olealkonium chloride, phenyltrimethicone, pantethine, panthenylethylether, silicone quaternium, keratin amino acids, polyquaternium, and any combinations thereof,
   wherein the composition has a ratio of crosslinking component to conditioning component in the range of about 10:90 to about 95:5, and
   wherein the composition has a pH range of between about 3.0 to about 8.5, and
   wherein said inorganic fluoride forms a crosslinked complex with the hair of a user when applied to the hair.

2. The composition of claim 1, wherein said pH is between about 4.5 to about 5.5.

3. The composition of claim 1, wherein said crosslinking component further comprises at least one additional component selected from the group consisting of: a thickener, a preservative, a humectant, a pH adjuster, soothing agent, emollients, emulsifiers, fragrance and water.

4. The composition of claim 3, wherein said crosslinking component comprises:
   said preservative having a concentration in the range between about 0.2 to about 1%;
   said humectant having a concentration in the range between about 0.1 to about 1%; and
   said water to bring the concentration up to 100%.

5. The composition of claim 3, wherein said preservative is at least one selected from the group consisting of: phenoxyethanol, sorbitol, potassium sorbate, sodium sorbate, methyl paraben, propyl paraben, imidazolidynyl urea, and DMDM hydantoin.

6. The composition of claim 3, wherein said humectant is at least one selected from the group consisting of: glycerine, propylene glycol, dipropylene glycol, diglycerin, panthenol, sodium PCA, sugar alcohols, lecithin, hydrolyzed wheat proteins, hydrolyzed rice proteins, hydrolyzed keratin proteins, hydrolyzed silk proteins, lipids and polyols.

7. The composition of claim 3, wherein said thickener is at least one selected from the group consisting of: polysaccharide, cellulose, cellulose, derivatives, natural gums, natural polymers, synthetic polymers and inorganic gel mineral silicates.

8. The composition of claim 3, wherein said pH adjuster is at least one selected from the group consisting of: phosphoric acid, citric acid, tartaric acid, lactic acid, acetic acid, and bases that include sodium hydroxide, potassium hydroxide, sodium carbonate, ammonium hydroxide, isopropanolamine, and monoethanolamine.

9. The composition of claim 1, wherein said inorganic fluoride is present in said composition in an amount of between about 0.4 to about 1.25%.

10. The composition of claim 1, wherein said ratio of said crosslinking component to said conditioner component is about 75:25.

\* \* \* \* \*